(12) United States Patent
Perlin

(10) Patent No.: US 6,807,490 B1
(45) Date of Patent: Oct. 19, 2004

(54) METHOD FOR DNA MIXTURE ANALYSIS

(76) Inventor: Mark W. Perlin, 5904 Beacon St., Pittsburgh, PA (US) 15217

( * ) Notice: Subject to any disclaimer, the term of this patent is extended or adjusted under 35 U.S.C. 154(b) by 0 days.

(21) Appl. No.: 09/504,389

(22) Filed: Feb. 15, 2000

(51) Int. Cl.$^7$ .......................... G06F 19/00; C12Q 1/68; C12P 19/34; C12N 15/11
(52) U.S. Cl. .......................... 702/20; 435/6; 435/91.2; 536/23.1
(58) Field of Search .................. 702/20, 19; 435/6, 435/91.2; 536/91.2, 23.1; 524/504

(56) References Cited

U.S. PATENT DOCUMENTS 5,374,527 A * 12/1994 Grossman ...................... 435/6
5,759,369 A * 6/1998 Menchen et al. .......... 204/456

OTHER PUBLICATIONS

Clayton et al. Analysis and interpretation of mixed forensic stains using DNA STR profiling. Forensic Science International vol. 91 pp. 55–70 (1998).*
Gill et al, Interpreting Simple STR Mixtures using Allele Peak Areas, 1998, Forensic Science International, vol. 91, pp. 41–53.*
Evett et al, Taking Account of Peak Areas when Interpreting Mixed DNA Profiles, 1998, Journal of Forensic Sciences, vol. 43, No. 1, pp. 62–69.*
Perlin et al, Toward Fully Automated Genotyping: Genotyping Microsatellite Markers by Deconvolution, 1995, American Journal of Human Genet., vol. 57, pp. 1199–1210.*

* cited by examiner

*Primary Examiner*—John S. Brusca
(74) *Attorney, Agent, or Firm*—Ansel M. Schwartz

(57) ABSTRACT

The present invention pertains to a process for automatically analyzing nucleic acid samples. Specifically, the process comprises the steps of forming electrophoretic data of DNA samples with DNA ladders; comparing these data; transforming the coordinates of the DNA sample's data into DNA length coordinates; and analyzing the DNA sample in length coordinates. This analysis is useful for automating fragment analysis and quality assessment. The automation enables a business model based on usage, since it replaces (rather than assists) labor. This analysis also provides a mechanism whereby data generated on different instruments can be confidently compared. Genetic applications of this invention include gene discovery, genetic diagnosis, and drug discovery. Forensic applications include identifying people and their relatives, catching perpetrators, analyzing DNA mixtures, and exonerating innocent suspects.

14 Claims, 11 Drawing Sheets

1 ACQUIRE DATA
2 PROCESS SIGNAL
3 SEPARATE COLORS
4 REMOVE PRIMERS
5 TRACK SIZES
6 EXTRACT PROFILES
*FIG.1*
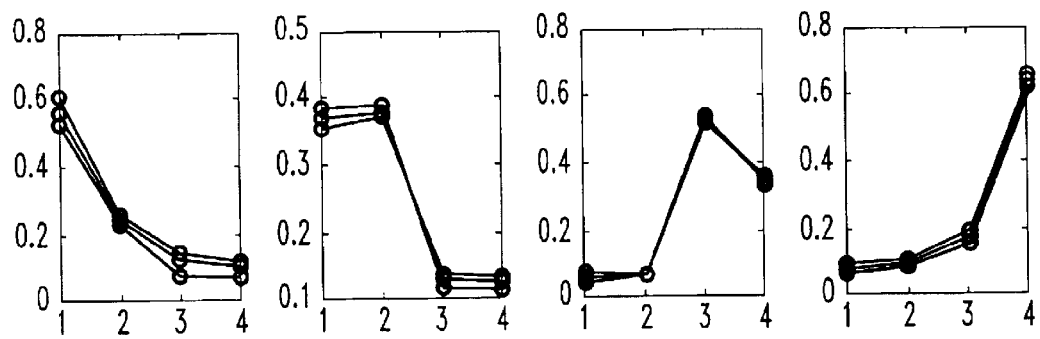
*FIG.2*
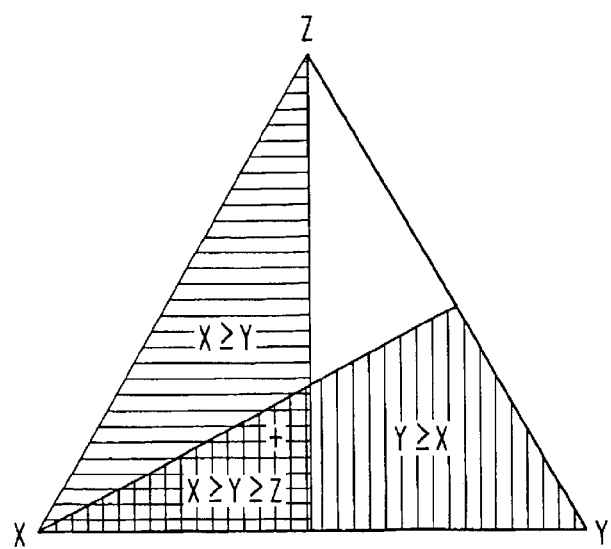
*FIG.3*

7 DERIVE ALLELIC LADDER
8 TRANSFORM COORDINATES
9 QUANTITATE TRACE
10 ANALYZE DATA

|    | A | B | C | D | E | F |
|----|---|---|---|---|---|---|
| 20 | | | | LABOR COST | | |
| 21 | PEOPLE COST | $1,024,000 | | | | |
| 22 | PER GENOTYPE | $1.02 | | | | |
| 23 | | | | | | |
| 24 | BREAKDOWN | PER PERSON | | | | |
| 25 | SALARY | $25,000 | | THROUGHPUT | PER DAY | PER YEAR |
| 26 | BENEFITS | $6,250 | | RUNS | 8 | 2,000 |
| 27 | SPACE | $2,000 | | GENOTYPES | 4,000 | 1,000,000 |
| 28 | COMPUTER | $2,000 | | | | |
| 29 | SOFTWARE | $10,000 | | SCORING | | |
| 30 | MANAGEMENT | $6,250 | | CALLS/PERSON | 500 | 125,000 |
| 31 | OVERHEAD | $12,500 | | PEOPLE | 16 | |
| 32 | COST | $64,000 | | | | |
| 33 | | | | ASSUMPTIONS | | |
| 34 | ASSUMPTIONS | | | GENOTYPES/RUN | 500 | |
| 35 | BENEFITS RATE | 0.25 | | DAYS/YEAR | 250 | |
| 36 | SQFEET/PERSON | 100 | | PEOPLE/CALL | 2 | |
| 37 | COST/SQFOOT YR | $20 | | | | |
| 38 | MANAGING RATE | 0.25 | | | | |
| 39 | OVERHEAD RATE | 0.50 | | | | |
| 40 | | | | | | |

*FIG. 13*

METHOD FOR DNA MIXTURE ANALYSIS

FIELD OF THE INVENTION

The present invention pertains to a process for analyzing a DNA molecule. More specifically, the present invention is related to performing experiments that produce quantitative data, and then analyzing these data to characterize a DNA fragment. The invention also pertains to systems related to this DNA fragment information.

BACKGROUND OF THE INVENTION

With the advent of high-throughput DNA fragment analysis by electrophoretic separation, many useful genetic assays have been developed. These assays have application to genotyping, linkage analysis, genetic association, cancer progression, gene expression, pharmaceutical development, agricultural improvement, human identity, and forensic science.

However, these assays inherently produce data that have signficant error with respect to the size and concentration of the characterized DNA fragments. Much calibration is currently done to help overcome these errors, including the use of in-lane molecular weight size standards. In spite of these improvements, the variability of these properties (between different instruments, runs, or lanes) can exceed the desired tolerance of the assays.

Recently, advances have been made in the automated scoring of genetic data. Many naturally occurring artifacts in the amplification and separation of nucleic acids can be eliminated through calibration and mathematical processing of the data on a computing device (M W Perlin, M B Burks, R C Hoop, and E P Hoffman, "Toward fully automated genotyping: allele assignment, pedigree construction, phase determination, and recombination detection in Duchenne muscular dystrophy," Am. J. Hum. Genet., vol. 55, no. 4, pp. 777–787, 1994; M W Perlin, G Lancia, and S-K Ng, "Toward fully automated genotyping: genotyping microsatellite markers by deconvolution," Am. J. Hum. Genet., vol. 57, no. 5, pp. 1199–1210, 1995; S-K Ng, "Automating computational molecular genetics: solving the microsatellite genotyping problem," Carnegie Mellon University, Doctoral dissertation CMU-CS-98-105, Jan. 23, 1998), incorporated by reference.

This invention pertains to the novel use of calibrating data and mathematical analyses to computationally eliminate undesirable data artifacts in a nonobvious way. Specifically, the use of allelic ladders and coordinate transformations can help an automated data analysis system better reduce measurement variability to within a desired assay tolerance. This improved reproducibility is useful in that it results in greater accuracy and more complete automation of the genetic assays, often taking less time at a lower cost with fewer people.

Genotyping Technology

Genotyping is the process of determining the alleles at an individual's genetic locus. Such loci can be any inherited DNA sequence in the genome, including protein-encoding genes and polymorphic markers. These markers include short tandem repeat (STR) sequences, single-nucleotide polymorphism (SNP) sequences, restriction fragment length polymorphism (RFLP) sequences, and other DNA sequences that express genetic variation (G Gyapay, J Morissette, A Vignal, C Dib, C Fizames, P Millasseau, S Marc, G Bernardi, M Lathrop, and J Weissenbach, "The 1993–94 Genethon Human Genetic Linkage Map," Nature Genetics, vol. 7, no. 2, pp. 246–339, 1994; P W Reed, J L Davies, J B Copeman, S T Bennett, S M Palmer, L E Pritchard, S C L Gough, Y Kawaguchi, H J Cordell, K M Balfour, S C Jenkins, E E Powell, A Vignal, and J A Todd, "Chromosome-specific microsatellite sets for fluorescence-based, semi-automated genome mapping," Nature Genet., vol. 7, no. 3, pp. 390–395, 1994; L Kruglyak, "The use of a genetic map of biallelic markers in linkage studies," Nature Genet., vol. 17, no. 1, pp. 21–24, 1997; D Wang, J Fan, C Siao, A Berno, P Young, R Sapolsky, G Ghandour, N Perkins, E Winchester, J Spencer, L Kruglyak, L Stein, L Hsie, T Topaloglou, E Hubbell, E Robinson, M Mittmann, M Morris, N Shen, D Kilburn, J Rioux, C Nusbaum, S Rozen, T Hudson, and E Lander, "Large-scale identification, mapping, and genotyping of single-nucleotide polymorphisms in the human genome," Science, vol. 280, no. 5366, pp. 1077–82, 1998; P Vos, R Hogers, M Bleeker, M Reijans, T van de Lee, M Hornes, A Frijters, J Pot, J Peleman, M Kuiper, and M Zabeau, "AFLP: a new technique for DNA fingerprinting," Nucleic Acids Res, vol. 23, no. 21, pp. 4407–14, 1995; J Sambrook, E F Fritsch, and T Maniatis, Molecular Cloning, Second Edition. Plainview, N.Y.: Cold Spring Harbor Press, 1989), incorporated by reference.

The polymorphism assay is typically done by characterizing the length and quantity of DNA from an individual at a marker. For example, STRs are assayed by polymerase chain reaction (PCR) amplification of an individual's STR locus using a labeled PCR primer, followed by size separation of the amplified PCR fragments. Detection of the fragment labels, together with in-lane size standards, generates a signal that permits characterization of the size and quantity of the DNA fragments. From this characterization, the alleles of the STR locus in the individual's genome can be determined (J Weber and P May, "Abundant class of human DNA polymorphisms which can be typed using the polymerase chain reaction," Am. J. Hum. Genet., vol. 44, pp. 388–396, 1989; J S Ziegle, Y Su, K P Corcoran, L Nie, P E Mayrand, L B Hoff, L J McBride, M N Kronick, and S R Diehl, "Application of automated DNA sizing technology for genotyping microsatellite loci," Genomics, vol. 14, pp. 1026–1031, 1992), incorporated by reference.

The labels can use radioactivity, fluorescence, infrared, or other nonradioactive labeling methods (F M Ausubel, R Brent, R E Kingston, D D Moore, J G Seidman, J A Smith, and K Struhl, ed., Current Protocols in Molecular Biology. New York, N.Y.: John Wiley and Sons, 1995; N J Dracopoli, J L Haines, B R Korf, C C Morton, C E Seidman, J G Seidman, D T Moir, and D Smith, ed., Current Protocols in Human Genetics. New York: John Wiley and Sons, 1995; L J Kricka, ed., Nonisotopic Probing, Blotting, and Sequencing, Second Edition. San Diego, Calif.: Academic Press, 1995), incorporated by reference.

Size separation of fragment molecules is typically done using gel or capillary electrophoresis (CE); newer methods include mass spectrometry and microchannel arrays (R A Mathies and X C Huang, "Capillary array electrophoresis: an approach to high-speed, high-throughput DNA sequencing," Nature, vol. 359, pp. 167–169, 1992; K J Wu, A Stedding, and C H Becker, "Matrix-assisted laser desorption time-of-flight mass spectrometry of oligonucleotides using 3-hydroxypicolinic acid as an ultraviolet-sensitive matrix," Rapid Commun. Mass Spectrom., vol. 7, pp. 142–146, 1993), incorporated by reference.

The label detection method is contingent on both the labels used and the size separation mechanism. For example, with automated DNA sequencers such as the PE Biosystems ABI/377 gel, ABI/310 single capillary or ABI/3700 capillary array instruments, the detection is done by laser scanning of the fluorescently labeled fragments, imaging on a CCD camera, and electronic acquisition of the signals from the CCD camera. Flatbed laser scanners, such as the Molecular Dynamics Fluorimager or the Hitachi FMBIO/II acquire flourescent signals similarly. Li-Cor's infrared automated sequencer uses a detection technology modified for the infrared range. Radioactivity can be detected using film or phosphor screens. In mass spectrometry, the atomic mass can be used as a sensitive label. See (A. J. Kostichka, Bio/Technology, vol. 10, pp. 78, 1992), incorporated by reference.

Size characterization is done by comparing the sample fragment's signal in the context of the size standards. By separate calibration of the size standards used, the relative molecular size can be inferred. This size is usually only an approximation to the true size in base pair units, since the size standards and the sample fragments generally have different chemistries and electrophoretic migration patterns (S-K Ng, "Automating computational molecular genetics: solving the microsatellite genotyping problem," Carnegie Mellon University, Doctoral dissertation CMU-CS-98-105, Jan. 23, 1998), incorporated by reference.

Quantitation of the DNA signal is usually done by examining peak heights or peak areas. One inexact peak area method simply records the area under the curve; this approach does not account for band overlap between different peaks. It is often useful to determine the quality (e.g., error, accuracy, concordance with expectations) of the size or quantity characterizations. See (D R Richards and M W Perlin, "Quantitative analysis of gel electrophoresis data for automated genotyping applications," Amer. J. Hum. Genet., vol. 57, no. 4 Supplement, pp. A26, 1995), incorporated by reference.

The actual genotyping result depends on the type of genotype, the technology used, and the scoring method. For example, with STR data, following size separation and characterization, the sizes (exact, rounded, or binned) of the two tallest peaks might be used as the alleles. Alternatively, PCR artifacts (e.g., stutter, relative amplification) can be accounted for in the analysis, and the alleles determined after mathematical corrections have been applied. See (M W Perlin, "Method and system for genotyping," U.S. Pat. No. 5,541,067, Jul. 30, 1996; M W Perlin, "Method and system for genotyping," U.S. Pat. No. 5,580,728, Dec. 3, 1996), incorporated by reference.

Genotyping Applications

Genotyping data can be used to determine how mapped markers are shared between related individuals. By correlating this sharing information with phenotypic traits, it is possible to localize a gene associated with that inherited trait. This approach is widely used in genetic linkage and association studies (J Ott, Analysis of Human Genetic Linkage, Revised Edition. Baltimore, Md.: The Johns Hopkins University Press, 1991; N Risch, "Genetic Linkage and Complex Diseases, With Special Reference to Psychiatric Disorders," Genet. Epidemiol., vol. 7, pp. 3–16, 1990; N Risch and K Merikangas, "The future of genetic studies of complex human diseases," Science, vol. 273, pp. 1516–1517, 1996), incorporated by reference.

Genotyping data can also be used to identify individuals. For example, in forensic science, DNA evidence can connect a suspect to the scene of a crime. DNA databases can provide a repository of such relational information (C P Kimpton, P Gill, A Walton, A Urquhart, E S Millican, and M Adams, "Automated DNA profiling employing multiplex amplification of short tandem repeat loci," PCR Meth. Appl., vol. 3, pp. 13–22, 1993; J E McEwen, "Forensic DNA data banking by state crime laboratories," Am. J. Hum. Genet., vol. 56, pp. 1487–1492, 1995; K Inman and N Rudin, An Introduction to Forensic DNA Analysis. Boca Raton, Fla.: CRC Press, 1997; C J Fregeau and R M Fourney, "DNA typing with fluorescently tagged short tandem repeats: a sensitive and accurate approach to human identification," Biotechniques, vol. 15, no. 1, pp. 100–119, 1993), incorporated by reference.

Linked genetic markers can help predict the risk of disease. In monitoring cancer, STRs are used to assess microsatellite instability (MI) and loss of heterozygosity (LOH)—chromosomal alterations that reflect tumor progression. (ID Young, Introduction to Risk Calculation in Genetic Counselling. Oxford: Oxford University Press, 1991; L Cawewell, L Ding, F A Lewis, I Martin, M F Dixon, and P Quirke, "Microsatellite instability in colorectal cancer: improved assessment using fluorescent polyterase chain reaction," Gastroenterology, vol. 109, pp. 465–471, 1995; F Canzian, A Salovaara, P Kristo, R B Chadwick, L A Aaltonen, and A de la Chapelle, "Semiautomated assessment of loss of heterozygosity and replication error in tumors," Cancer Research, vol. 56, pp. 3331–3337, 1996; S Thibodeau, G Bren, and D Schaid, "Microsatellite instability in cancer of the proximal colon," Science, vol. 260, no. 5109, pp. 816–819, 1993), incorporated by reference.

For crop and animal improvement, genetic mapping is a very powerful tool. Genotyping can help identify useful traits of nutritional or economic importance. (H J Vilkki, D J de Koning, K Elo, R Velmala, and A Maki-Tanila, "Multiple marker mapping of quantitative trait loci of Finnish dairy cattle by regression," J. Dairy Sci., vol. 80, no. 1, pp. 198–204, 1997; S M Kappes, J W Keele, R T Stone, R A McGraw, T S Sonstegard, T P Smith, N L Lopez-Corrales, and C W Beattie , "A second-generation linkage map of the bovine genome," Genome Res., vol. 7, no. 3, pp. 235–249, 1997; M Georges, D Nielson, M Mackinnon, A Mishra, R Okimoto, A T Pasquino, L S Sargeant, A Sorensen, M R Steele, and X Zhao, "Mapping quantitative trait loci controlling milk production in dairy cattle by exploiting progeny testing," Genetics, vol. 139, no. 2, pp. 907–920, 1995; G A Rohrer, d J Alexander, Z Hu, T P Smith, J W Keele, and C W Beattie, "A comprehensive map of the porcine genome," Genome Res., vol. 6, no. 5, pp. 371–391, 1996; J Hillel, "Map-based quantitative trait locus identification," Poult. Sci., vol. 76, no. 8, pp. 1115–1120, 1997; H H Cheng, "Mapping the chicken genome," Poult. Sci., vol. 76, no. 8, pp. 1101–1107, 1997), incorporated by reference.

Other Sizing Assays

Fragment analysis finds application in other genetic methods. Often fragment sizes are used to multiplex many experiments into one shared readout pathway, where size (or size range) serves an index into post-readout demultiplexing. For example, multiple genotypes are typically pooled into a single lane for more efficient readout. Quantifying information can help determine the relative amounts of nucleic acid products present in tissues. (G R Taylor, J S Noble, and R F Mueller, "Automated analysis of multiplex microsatellites," J. Med. Genet, vol. 31, pp. 937–943, 1994; L S Schwartz, J Tarleton, B Popovich, W K Seltzer, and E P Hoffmn, "Fluorescent multiplex linkage analysis and carrier detection for Duchenne/Becker muscular dystrophy," Am. J. Hum. Genet., vol. 51, pp. 721–729, 1992; C P Kimpton, P Gill, A Walton, A Urquhart, E S Millican, and M Adams, "Automated DNA profiling employing multiplex amplification of short tandem repeat loci," PCR Meth. Appl., vol. 3, pp. 13–22, 1993), incorporated by reference.

Differential display is a gene expression assay. It performs a reverse transcriptase PCR (RT-PCR) to capture the state of expressed mRNA olecules into a more robust DNA form. These DNAs are then size separated, and the size bins provide an index into particular molecules. Variation at a size bin between two tissue assays is interpreted as a concommitant variation in the underlying mRNA gene expression profile. A peak quantification at a bin estimates the underlying mRNA concentration. Comparison of the quantitation of two different samples at the same bin provides a measure of relative up- or down-regulation of gene expression. (S W Jones, D Cai, O S Weislow, and B Esmaeli-Azad, "Generation of multiple mRNA fingerprints using fluorescence-based differential display and an automated DNA sequencer," BioTechniques, vol. 22, no. 3, pp. 536–543, 1997; P Liang and A Pardee, "Differential display of eukaryotic messenger RNA by means of the polymerase chain reactions," Science, vol. 257, pp. 967–971, 1992; K R Luehrsen, L L Marr, E van der Knaap, and S Cumberledge, "Analysis of differential display RT-PCR products using fluorescent primers and Genescan software," BioTechniques, vol. 22, no. 1, pp. 168–174, 1997), incorporated by reference.

Single stranded conformer polymorphism (SSCP) is a method for detecting different mutations in a gene. Single base pair changes can markedly affect fragment mobility of the conformer, and these mobility changes can be detected in a size separation assay. SSCP is of particular use in identifying and diagnosing genetic mutations (M Orita, H Iwahana, H Kanazawa, K Hayashi, and T Sekiya, "Detection of polymorphisms of human DNA by gel electrophoresis as single-strand conformation polymorphisms," Proc Natl Acad Sci USA, vol. 86, pp. 2766–2770, 1989), incorporated by reference.

The AFLP technique provides a very powerful DNA fingerprinting technique for DNAs of any origin or complexity. AFLP is based on the selective PCR amplification of restriction fragments from a total digest of genomic DNA. The technique involves three steps: (i) restriction of the DNA and ligation of oligonucleotide adapters, (ii) selective amplification of sets of restriction fragments, and (iii) gel analysis of the amplified fragments. PCR amplification of restriction fragments is achieved by using the adapter and restriction site sequence as target sites for primer annealing. The selective amplification is achieved by the use of primers that extend into the restriction fragments, amplifying only those fragments in which the primer extensions match the nucleotides flanking the restriction sites. Using this method, sets of restriction fragments may be visualized by PCR without knowledge of nucleotide sequence. The method allows the specific co-amplification of high numbers of restriction fragments. The number of fragments that can be analyzed simultaneously, however, is dependent on the resolution of the detection system. Typically 50–100 restriction fragments are amplified and detected on denaturing polyacrylamide gels. (P Vos, R Hogers, M Bleeker, M Reijans, T van de Lee, M Hornes, A Frijters, J Pot, J Peleman, M Kuiper, and M Zabeau, "AFLP: a new technique for DNA fingerprinting," *Nucleic Acids Res*, vol. 23, no. 21, pp. 4407–14, 1995), incorporated by reference.

Data Scoring

The final step in any fragment assay is scoring the data. This is typically done by having people visually review every experiment. Some systems (e.g., PE Informatics' Genotype program) perform an initial computer review of the data, to make the manual visual review of every genotype easier. More advanced systems (e.g., Cybergenetics' TrueAllele technology) fully automate the data review, and provide data quality scores that can be used to identify data artifacts (for eliminating such data from consideration) and rank the data scores (to focus on just the 2%–25% of suspect data calls). See (B Palsson, F Palsson, M Perlin, H Gubjartsson, K Stefansson, and J Gulcher, "Using quality measures to facilitate allele calling in high-throughput genotyping," Genome Research, vol. 9, no. 10, pp. 1002–1012, 1999; M W Perlin, "Method and system for genotyping," U.S. Pat. No. 5,876,933, Mar. 2, 1999), incorporated by reference.

However, even with such advanced scoring technology, artifacts can obscure the results. More importantly, insufficient data calibration can preclude the achievement of very low (e.g., <1%) data error rates, regardless of the scoring methods. For example, in high-throughput STR genotyping, differential migration of a sample's PCR fragments relative to the size standards can produce subtle shifts in detected size. This problem is worse when different instruments are used, or when size separation protocols are not entirely uniform. The result is that fragments can be incorrectly assigned to allele bins in a way that cannot be corrected without recourse to additional information (e.g., pedigree data) completely outside the STR sizing assay.

Whole System

This invention centers on a new way to greatly reduce sizing and quantitation errors in fragment analysis. By designing data generation experiments that include the proper calibration data (e.g., internal lane standards, allelic ladders, uniform run conditions), most of these fragment analysis errors can be eliminated entirely. Moreover, computer software can be devised that fully exploits these data calibrations to automatically identify artifacts and rank the data by quality. The result is a largely error-free system that requires minimal (if any) human intervention.

SUMMARY OF THE INVENTION

The present invention pertains to a method for analyzing a nucleic acid sample. The method comprises the steps of forming labeled DNA sample fragments from a nucleic acid sample. Then there is the step of size separating and detecting said sample fragments to form a sample signal. Then there is the step of forming labeled DNA ladder fragments corresponding to molecular lengths. Then there is the step of size separating and detecting said ladder fragments to form a ladder signal. Then there is the step of transforming the sample signal into length coordinates using the ladder signal. Then there is the step of analyzing the nucleic acid sample signal in length coordinates.

The present invention also pertains to a system for analyzing a nucleic acid sample. The system comprises means for forming labeled DNA sample fragments from a nucleic acid sample. The system further comprises means for size separating and detecting said sample fragments to form a sample signal, said separating and detecting means in communication with the sample fragments. The system further comprises means for forming labeled DNA ladder fragments corresponding to molecular lengths. The system further comprises means for size separating and detecting said ladder fragments to form a ladder signal, said separating and detecting means in communication with the ladder fragments. The system further comprises means for transforming the sample signal into length coordinates using the ladder signal, said transforming means in communication with the signals. The system further comprises means for analyzing the nucleic acid sample signal in length coordinates, said analyzing means in communication with the transforming means.

The present invention also pertains to a method for generating revenue from computer scoring of genetic data. The method comprises the steps of supplying a software program that automatically scores genetic data. Then there is the step of forming genetic data that can be scored by the software program. Then there is the step of scoring the genetic data using the software program to form a quantity of genetic data. Then there is the step of generating a revenue from computer scoring of genetic data that is related to the quantity.

The present invention also pertains to a method for producing a nucleic acid analysis. The method comprises the steps of analyzing a first nucleic acid sample on a first size separation instrument to form a first signal. Then there is the step of analyzing a second nucleic acid sample on a second size separation instrument to form a second signal. Then there is the step of comparing the first signal with the second signal in a computing device with memory to form a comparison. Then there is the step of producing a nucleic acid analysis of the two samples from the comparison that is independent of the size separation instruments used.

The present invention also pertains to a method for resolving DNA mixtures. The method comprises the steps of obtaining DNA profile data that include a mixed sample. Then there is the step of representing the data in a linear equation. Then there is the step of deriving a solution from the linear equation. Then there is the step of resolving the DNA mixture from the solution.

BRIEF DESCRIPTION OF THE DRAWINGS

FIG. 1 shows the steps of creating sized profiles.

FIG. 2 shows unimodal plots, each corresponding to a fluorescent dye; within each plot, intensity is plotted against the sampled spectrum.

FIG. 3 shows the unimodality constraint determining the function space geometry of the spectrum sampling vectors.

FIG. 13 shows a spreadsheet for calculating the labor cost of scoring genetic data.

DESCRIPTION OF THE PREFERRED EMBODIMENT

Data Generation

Figure 4:
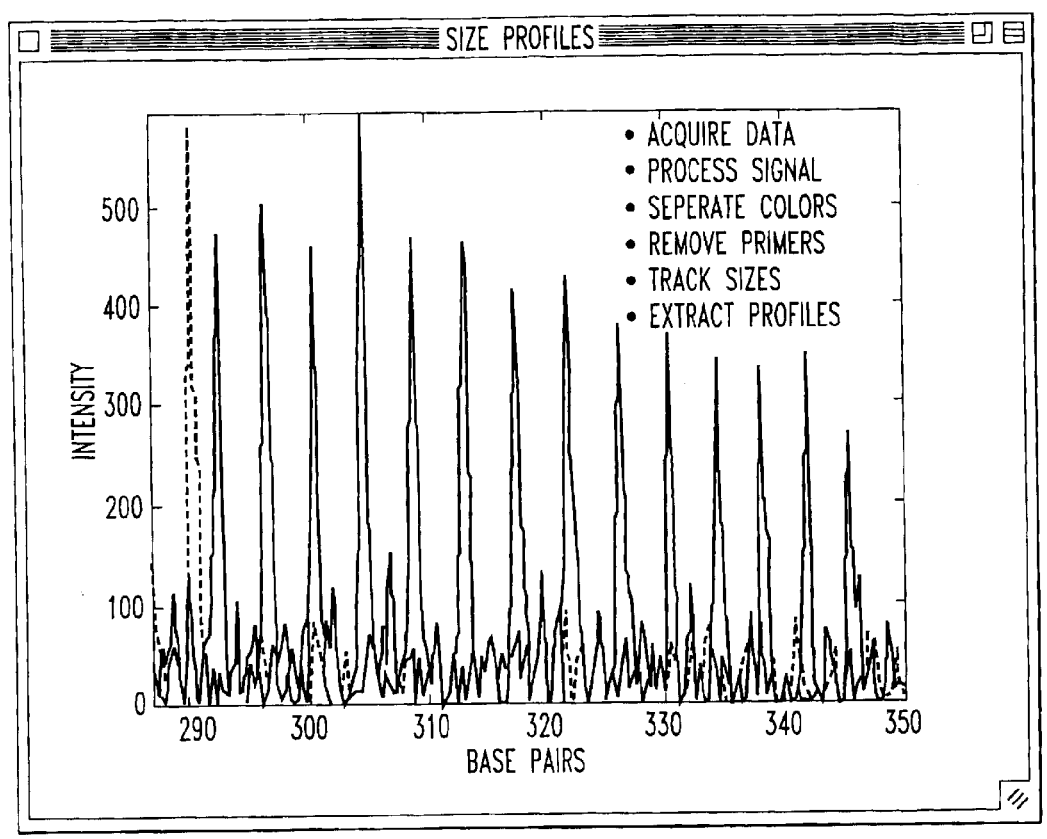
FIG. 4 shows the results of signal processing, size tracking, and size transformation.

In the most preferred embodiment, genotyping data is generated using STR markers. These tandem repeats include mono-, di-, tri-, tetra-, penta-, hexa-, hepta-, octa-, nona-, deca- (and so on) nucleotide repeat elements. STRs are highly abundant and informative marker distributed throughout the genomes of many species (including human). Typically, STRs are labeled, PCR amplified, and then detected (for size and quantity) on an electrophoretic gel.

The laboratory processing starts with the acquisition of a sample, and the extraction of its DNA. The extraction and purification are typically followed by PCR amplification. Labelling is generally done using a 5' labeled PCR primer, or with incorporation labeling in the PCR. Prior to loading, multiple marker PCR products in k—1 different fluorescent colors are pooled, and size standards (preferably in a $k^{th}$ different color) is added. Size separation and detection is preferably done using automated fluorescent DNA sequencers, with either slab gel or capillary technology. The detected signals represent the progression of DNA bands as a function of time. These signals are transmitted from the sequencer to a computing device with memory, where they are stored in a file. (N J Dracopoli, J L Haines, B R Korf, C C Morton, C E Seidman, J G Seidman, D T Moir, and D Smith, ed., Current Protocols in Human Genetics. New York: John Wiley and Sons, 1995), incorporated by reference.

To create STR allelic ladders, the most preferred embodiment entails PCR amplification of pooled samples. This can be done by preparing DNA from N (preferably, N is between 2 and 200, depending on the application) individuals in equimolar 3 ng/ul concentrations. These DNAs are then pooled. After dilution, each PCR template contains contains 48 ng of DNA in an 18 ul volume, and is included in a standard 50 ul PCR containing 2.5 units of Amplitaq Gold, 1.25 ul of each primer, 200 uM dNTP's, and 2.5 mM $MgCl_2$. This mixture is then PCR amplified with its STR primers (one labeled) on a thermocycler (e.g., with an MJ Research PTC-100, use 30 cycles of 94° C. for 1.25', 55° C. for 1', and 72° C. for 1'). Size separation of the PCR products on an ABI sequencer includes internal lane size standards (GS500 ROX-labeled 50 bp sizing ladder, Perkin-Elmer, Foster City, Calif.; 20 bp MapMarkers sizing ladder, BioVentures, Murfreesboro, Tenn.). Files are similarly recorded from this experiment.

In an alternative preferred embodiment, multiplexed SNP data is generated using size standards with standard protocols. Typically, each size bin in the electrophoretic signal corresponds to one marker or polymorphism. Presence in the size bin of a signal of sufficient strength and correct color indicates the presence of an allele; absence of the signal indicates allele absence. Signal size and color establish the allele, while signal strength determines the amount of DNA present (if any). (N J Dracopoli, J L Haines, B R Korf, C C Morton, C E Seidman, J G Seidman, D T Moir, and D Smith, ed., Current Protocols in Human Genetics. New York: John Wiley and Sons, 1995), incorporated by reference.

In another alternative preferred embodiment, differential display data is generated, preferably as follows: Making cDNA. The mRNA differential display reverse transcription-polymerase chain reaction (DDRT-PCR) is performed using reagents supplied in a RNAimage™ kit (GeneHunter Corp, Nashville, Tenn.). RNA duplicates from two tissue samples are reverse-transcribed using oligo(dT) primers and MMLV reverse transcriptase (RTase). For a 20 ul reaction, adding (in order) 9.4 ul of $H_2O$, 4 ul of 5×reaction buffer, 1.6 ul of 250 uM each dNTPs, 2 ul of 2 uM one oligo(dT) primer (H-T11M: M is G, C, or A), and 2 ul of 0.1 ug/ul DNA-free total RNA. The RT reactions are run on a thermocycler (e.g., NJ Research, 65° C. for 5 min, 37° C. for 60 min, and 75°

C. for 5 min). MMLV RTase (1 ul, 100 units) are added in the reaction after incubation for 10 min at 37° C. A control is included without adding RTase. Amplification and labeling. For a 20 ul PCR reaction, add 9.2 ul of $H_2O$, 4 ul of 10×PCR buffer, 1.6 ul of 25 uM each dNTPs, 2 ul of 2 uM H-T11M oligo(dT) primer, 2 ul of 2 uM of arbitrary primer (AP), 2 ul of corresponding H-T11M reverse transcribed cDNA, and 0.2 ul (1 unit) of AmpliTaq DNA polymerase (Perkin Elmer, Norwalk, Conn.). Each of the three different H-T11M PCR primers are labeled with its own spectrally distinct fluorescent dye, such as FAM, HEX, and NED. The cDNAs are randomly amplified by low-stringency PCR (40 cycles with temperature at 94° C. for 15 sec, 40° C. for 2 min, and 72° C. for 2 min) in an MJR PCT/100 thermocycler. A final extension is performed at 72° C. for 10 min. Samples (without added RTase or CDNA) are simultaneously tested as controls. Multiple primer sets can be used. For example, 24 sets of primers (8 AP×3 H-T11M) are used in each kit; using 10 kits for screening differentially expressed cDNA tags produces 240 reactions per tissue. Size separation. Size standards in another dye are then added to the amplified labeled products, and then size separated on a manual or automated sequencing gel (or capillary) instrument. Differential display data generation protocols have been well described (N J Dracopoli, J L Haines, B R Korf, C C Morton, C E Seidman, J G Seidman, D T Moir, and D Smith, ed., Current Protocols in Human Genetics. New York: John Wiley and Sons, 1995), incorporated by reference.

There are other alternative preferred embodiments for generating DNA fragment data whose assay includes a size separation, such as Amplification Refractory Mutation System (ARMS), Single-Strand Conformation Polymorphism (SSCP), Restriction Fragment Length Polymorphism (RFLP), and Amplified Fragment Length Polymorphism (AFLP). These have been enumerated, with associated protocols (N J Dracopoli, J L Haines, B R Korf, C C Morton, C E Seidman, J G Seidman, D T Moir, and D Smith, ed., Current Protocols in Human Genetics. New York: John Wiley and Sons, 1995; ABI/377 and ABI/310 GeneScan Software and Operation Manuals, PE Biosytems, Foster City, Calif.), incorporated by reference.

Extracting Profiles

Once DNA fragment sizing data have been generated, the data are then analyzed to characterize the and quantity of the component fragments.

Referring to FIG. 1, Step 1 is for acquiring the data.

The process begins by reading in the generated data from their native file formats, as defined by the DNA sequencer manufacturer. Let n be the number of lanes or capillaries, and m be the number of frequency acquisition channels. Capillary machines typically produce files where each file represents either all m channels of one capillary, or one channel of one capillary. Gel-based instruments typically produce files where one file represents either all m channels of the entire image, or one channel of one image. Intermediate cases, with the number of channels per file between 1 and m, can occur as well. once the signals have been read in, capillary input data signals are preferably stored in an n×m structure of one dimensional arrays in the memory of a computing device. This structure contains the signal profiles, with each array element corresponding to one channel of one capillary. Gel data are preferably stored as m two dimensional data arrays, one for each acquisition frequency.

The computer software preferably integrates with current sequencer and CE technology. It preferably has two manufacturer-independent input modules: one for sequencer gel data (e.g., PE Biosystems ABI/377, Molecular Dynamics Fluorimager), and one for CE data (e.g., PE Biosystems ABI/310, SpectruMedix SCE/9600). These modules are extensible and flexible, and preferably handle any known sequencer or CE data in current (or future) file formats.

Referring to FIG. 1, Step 2 is for processing the signal.

In this step, basic signal processing is done, such as baseline removal or filtering (e.g., smoothing) the data.

In the preferred embodiment for one dimensional signals, baseline removal is done using a sliding window technique. Within each window (of, say, 10 to 250 pixels, depending on the average number of pixel samples per base pair units), a minimum value is identified. Using overlapping windows, a cubic spline is fit through the minimum points, creating a new baseline function that describes the local minima in each window neighborhood. To remove the baseline, this new baseline function is subtracted away from the original function.

In the preferred embodiment for two dimensional images, the baseline is removed as follows. A local neighborhood overlapping tiling is imposed on the image, and minimum values identified. Create a baseline surface from these local minima, and subtract this baseline surface from the image to remove the baseline from the image.

In the preferred embodiment, filtering and other smoothing is done using convolution. A convolution kernel (such as a gaussian or a binomial function) is applied across the one dimensional capillary signal, or the two dimensional scanned gel image. The radius of smoothing depends on number of pixels per base pair unit—denser sampling requires less smoothing. However, with overly dense sampling, the data size can be reduced by filtering out redundant points.

Referring to FIG. 1, Step 3 is for separating the colors.

A key element of fluorescent genetic analysis is separating the fluorescent dye signals. In the current art, this is done by:

(1) Performing a dye standard calibration experiment using known dyes, often in separate lanes. A (dye color vs. frequency detection) classification matrix C is known directly from which dye is used. Each column of C contains a "1" in the row corresponding to the known color, with all other entries set to "0".

(2) Measuring the signals at separate fluorescent detection frequencies. These frequencies correspond to the "filter set" of the sequencer. For each pure dye peak, the signals that are measured across all the detection frequencies reveal the "bleedthrough" pattern of one dye color into its neighboring frequencies. Each pattern is normalized, and stored as a column in a data matrix D. The $j^{th}$ column of D is the "spectral bleedthrough" system response to the impulse input function represented in the $j^{th}$ column of C.

(3) The relationship between C and D is described by the linear response dye calibration matrix M as:

$$D = M \times C$$

To determine the unknown dye calibration matrix M (or its inverse matrix $M^{-1}$) from the data, apply matrix division, e.g., using singular value decomposition (SVD), to the matrices C and D. For example, this SVD operation is built into the MATLAB programming language (The MathWorks, Inc., Natick, Mass.), and has been described (W H Press, S A Teukolsky, W T Vetterling, and B P Flannery, Numerical Recipes in C: The Art of Scientific Computing, Second Edition. Cambridge: Cambridge University Press, 1992), incorporated by reference.

(4) Thereafter, the spectral overlap is deconvolved on new unknown data D' to recover the original dye colors C'. This is done by computing:

$$C' = M^{-1} \times D'$$

While the current art enables the color separation step, it is not ideal. Slight variations in the gel (e.g., thickness, composition, temperature, chemistry) and the detection unit (e.g., laser, CCD, optics) can contribute to larger variations in fluorescent response. An operator may encounter the following problems:

Calibrating the correction matrix $M^{-1}$ on one gel run does not necessarily model the "spectral bleedthrough" pattern accurately on future runs.

With 96 (or other multi-) capillary electrophoresis, each of the capillaries forms its own gel system, whose different properties may necessitate a separate calibration matrix.

Accurate dye calibration is technically demanding, labor intensive, time consuming, and expensive. Moreover, it can introduce considerable error into the system, particularly when the manual procedure is not carried out correctly. In such cases, the correction is imperfect and artifacts can enter the system.

Such color "bleedthrough" (also termed "crosstalk" or "pullup") artifacts can severely compromise the utility of the acquired data. In some cases, the gels must be rerun. Often scientific personnel waste considerable time examining highly uninformative data.

In one preferred embodiment, the color matrix is calibrated directly from the data, without recourse to separate calibration runs. This bleedthrough artifact removal is done using computer algorithms for the calibration, rather than manually conducting additional calibration experiments. This can be done using methods developed for DNA sequence analysis based on general data clustering. While such clustering methods require relatively large amounts of data, they can be effective (W Huang, Z Yin, D Fuareann, D States, and L Thomas Jr, "A method to determine the filter matrix in four-dye fluorescence-based DNA sequencing," Electrophoresis, vol. 18, no. 1, pp. 23–5, 1997; Z Yin, J Severin, M Giddings, W Huang, M Westphall, and L Smith, "Automatic matrix determination in four dye fluorescence-based DNA sequencing," Electrophoresis, vol. 17, no. 6, pp. 1143–50, 1996), incorporated by reference.

It would be desirable to use the least amount of most certain data when determining a color matrix for separating dye colors. Note that in the matrix relation "D=M×C", the data columns D are known from experiment. When a calibration run is used, the 0/1 classification columns C are known; from these known values, the unknown M can be computed. However, when there is no calibration run, the classification matrix C must be dynamically determined from the data in order to compute M. This can be done manually by a user identifying peaks, or automatically by the general clustering embodiment. However, there is a more refined and novel approach to automatically classifying certain data peaks to their correct color.

The most preferred embodiment finds a $\{C, D\}$ matrix pair using minimal data. Thus, M (a nd $M^{-1}$) can be determined, and the rest of the new data color separated. This embodiment exploits a key physical fact about spectral emission curves: they are unimodal. Referring to FIG. 2, such curves monotonically rise up to a maximum value, and then monotonically decrease from that maximum. Therefore, when a peak is generated from a single dye color, spectrally sampled across a range of frequencies, and the intensities plotted as a function of frequency, the plotted curve demonstrates unimodal behavior—the curve rises up to a maximum intensity, and then decreases again. This physical "unimodality" constraint on single color peaks can serve as a useful choice function for automatically (and intelligently) choosing peak data for the classification matrix C.

The function space equivalent of a unimodal function has a very useful property. Suppose that m different frequency channels are sampled. That is, there are m frequencies $x = \{x_1, x_2, \ldots, x_m\}$ sampled in the spectral domain. An equivalent representation of the m-point function $f: \underline{m} \to \Re$ is as an m-vector $v = <x_1, X_2, \ldots, x_m>$ in the vector space $\Re^m$. Now, select an appropriate norm on this vector space (say, $L_1$ or $L_2$), and normalize the vector v relative to its length, forming $$w = \frac{v}{\|v\|}.$$

In an $L_1$ normalization, w lives on a flat simplex (in the all-positive simplex facet). In $L_2$, w lives on a corresponding curved surface.

The unimodality constraint on x imposes additional geometrical constraints on w. Because x is unimodal, note that $$x_1 \leq x_2 \leq \ldots \leq x_k,$$

and that $$x_k \geq x_{k+1} \geq \ldots \geq x_m,$$

where k is the index of the maximum value of x.

These inequality constraints determine the exact subfacet in which w must reside on the simplex facet. Consider the case of three spectral sampling points, where the three-dimensional vector $<x, y, z> \in \Re^3$, and suppose that the unimodal constraint is $x \geq y \geq z$, corresponding to the first dye color. Referring to FIG. 3, the locations x, y, and z designate the unit locations on the axes in $\Re^3$ (i.e., at <1,0,0>, <0,1,0>, and <0,0,1>, respectively). Here, the $x \geq y$ constraint produces one region (horizontal shading), the $y \geq z$ constraint another (vertical shading), and their intersection corresponds to the full constraint (crosshatch shading). Good calibration points for use as columns in a $\{C, D\}$ matrix pair will cluster (white circle) around the dye's actual sampling point ratio vector (black cross). Conversely, poor candidate calibration points will tend to lie outside the cluster, and can be rejected. This geometry in the function space permits selection of only the most consistent calibration data.

The procedure starts by gathering likely unimodal data (e.g., those with highest intensities) for a given observed color k. After normalization, these candidate calibration data $\{w_i\}$ will cluster within the same subfacet of a flat (m–1)-dimensional facet; this facet is the all-positive face of the m-dimensional simplex. This geometric constraint follows directly from the physical unimodality constraint of pure spectral curves. An entire class of simple and effective clustering algorithms are based around exploiting this geometric constraint.

In one preferred embodiment, choose as cluster center point $w_0$, the mean vector location of $\{w_i\}$; vector $w_0$ also lies on the simplex subfacet (FIG. 3). Then, a small inner product $<w_i, w_0>$ value tends to indicate close proximity of $w_i$ and $w_0$. Taking a small set (e.g., $1 \leq s \leq 20$) of the closest vectors $w_i$ near $w_0$ selects good calibration data points, all pre-classified to Q color k. To determine $M^{-1}$, for each color k, take at most s such clustering points $\{w_i\}$, and use the corresponding $\{v_i\}$ as columns in D, where $v_i$ is normalized with respect to the maximum element in $w_i$. Form a vector u that is all zeros, except for a 1 in the $k^{th}$ entry; place s copies of u as columns in matrix C. This produces the required calibration matrices C and D, from which M and its inverse are immediately computed using SVD or another matrix inversion algorithm.

In the most preferred color separation algorithm, the criterion for peak selection is based on minimizing the spectral width of the peaks. A good measure of peak width is the variance across the spectral sampling frequency points. The variance calculation can take into account the sampling frequencies actually used, if desired. In this procedure, the variances of candidate peaks for a given color frequency are computed. Those peaks having the smallest spectral variance indicate the best calibration points. In an alternative implementation, a best fit of the observed frequency curve with a known frequency curve (e.g., via a correlation or inner product maximization) can indicate the best points to use.

The method applies not only to raw data, but also to data that has been previously color separated by other (possibly inaccurate) color correction matrices. This is because the unimodality constraint generally applies to such data.

A useful feature of the unimodality approach is that the model can automatically select good calibration peaks, even with very sparse data. This is because the function space geometry effectively constrains the clustering geometry. Such sparse-data clustering algorithms are particularly useful with capillary data, where one capillary may only have 1 or 2 useful calibration peaks corresponding to a given color. Despite this data limitation, the method easily finds these peaks, and effectively separates the colors. Such automation enables customization of the dye separation matrix to each capillary on each run, which virtually eliminates the bleedthrough artifact.

It is useful to have a quality score that measures how well the computed matrix correction actually corrects the data. This can be done by comparing the expected vs. observed results; this comparison can be computed either the separated or unseparated domain. Using the computer-selected calibration data vectors D, if the computed correction matrix $M^{-1}$ is correct, then the 0/1 calibration matrix of column vectors C will be recomputed exactly from the data matrix D:

$$C'=M^{-1} \times D$$

where, theoretically, C'=C. Measuring the deviation between C and C' measures how well the correction worked. One straightforward deviation measure sums the normed $L_2$ deviations between each column of C' and its corresponding column in C. When the deviation is too great (e.g., due to failed PCR amplification), a matrix based on a more confident (manual or automatic) calibration can be used.

Referring to FIG. 1, Step 4 is for removing the primers.

When the separated DNA fragments are formed from labeled PCR primers, it useful to remove the intense primer signal prior to initiating quantitative analyses. There are many standard signal processing methods for removing a singularity from a signal, or a row of such large peaks from an image.

For one dimensional data, first detect the primer signal. This can be done, in one embodiment, by smoothing (i.e., low pass filtering) the signal to focus on broad variations, and then fitting the largest peak (i.e., the primer peak) to an appropriate function, such as a Gaussian. Determining the variance of the peak from the function fit provides the domain interval on which the primer peak should be removed. On this domain, it is most preferable to set the values on this interval to an appropriate background value (e.g., zero, if background substracted, or an average of neighboring values outside the interval). Alternatively, one can crop the interval from the signal.

For two dimensional data, a projection of the pixel data onto the vertical axis of DNA separation finds the row of peaks. Determine the spread of this peak signal by curve fitting (e.g., with a Gaussian). Remove the primer peaks by either cropping the signal from the image, or setting the values in that domain to zero (or some other appropriate background value). Referring to FIG. 1, Step 5 is for tracking the sizes.

In the preferred embodiment, size standards are run in the same lane as the sample data, and are labeled with a label different from the label used for the sample data. The task is to find these size standards peaks, confirm which peaks represent good size standard data, and then align the observed size standards peaks with the expected sizes of the size standards. This process creates a mapping between the size standard peak data sampled in the pixel domain, and the known sizes (say, in base pair or molecular weight units) of each peak.

For one dimensional data, there are no lateral lanes to help determine which of the peaks observed in the size standard signal represent good data. Therefore, a preferred procedure uses prior information about the size standards (e.g., the size) to ensure a proper matching of data peaks to known sizes. In the preferred embodiment, use the following steps:

0. Find some good candidate peaks to get started.
1. Identify the best peaks to use by filtering poor candidates. This can be done by performing quality checks (e.g., for the height, width, or peak fit) on the candidate peaks.
2. Match the expected peak locations to the observed data peaks. This is done by applying a "zipper match" algorithm to the best candidate data peaks and the expected sizes. This matching uses local extension to align the peaks with sizes, and includes the following steps:

2a. Match the boundary, that is, a subset of smallest size data peaks or largest size data peaks. The algorithm can be rerun several times, shifting the boundary data peaks or the expected sizes. The best boundary shift can be found by heuristic minimization. One good heuristic assesses the uniformity (e.g., by minimizing the variance) of the ratios across matching local intervals of the expected size standard difference to the observed data peak difference.

2b. Fix a tolerance interval that includes unity (different tolerance intervals can be tried).

2c. Starting with the (possibly truncated) boundaries of the expected sizes and observed peaks aligned, extend this boundary.

2d. Compute the ratio p of the difference between the next expected peak size and the current expected peak size, to the difference between the next observed peak size and the current observed peak size.

2e. Compute the ratio q of the difference between the current expected peak size and the previous expected peak size, to the difference between the current observed peak size and the previous observed peak size.

2f. If the ratio (p/q) is greater than the tolerance interval's greatest value, then the observed data peak falls short. Reject the observed data peak, advance to the next observed data peak, and continue.

2g. If the ratio (p/q) is less than the tolerance interval's least value, then the expected data size falls short. Reject the expected data size, advance to the next expected data size, and continue.

2h. If the ratio (p/q) lies within the tolerance interval, then the expected data size is well matched to the observed data peak. Accept the size and the peak, record their match, and advance to the next size and peak.

3. If desired, fill in any missing data peaks by interpolation with expected sizes from the zipper matching result.

4. Compute a quality score for the matching result. Useful scores include:

4a. Fitting the matching of the expected sizes (in base pair, or other expected unit) with the peak sizes (in pixels, or other observed data unit). The relationship is monotonic and typically slowly varying, so a deviation from a fitted function (e.g., linear, cubic, or Southern mobility relationship) works well.

4b. Another quality score is the number of size mismatches, adjusted by the boundary shift.

5. Report the peak positions, matched with size standards. It is also useful to include the quality score of the match.

For two dimensional gel data, proceed by tracking on the color-separated size standard image. To track simultaneously both the sizes and lanes, first focus on a boundary row (e.g., the top row) of size standards. Model the row geometry (e.g., curvature, size, location) and each of the peaks (e.g., height, shape, angle). Then use this pattern as a set of geometrical constraints for analyzing the next row. Use global search to find the next row, and more localized search to identify the peaks; refine the local peak locations using center-of-mass calculations. Continue this process iteratively until the size standard data are completely analyzed, and a final grid is produced. It is possible to use a prior analysis of the loading/run pattern as calibration data in order to speed up subsequent tracking. The output of this lane/size tracking is a mapping between the expected (lane, base pair size) coordinate grid, and the observed (x pixel, y pixel) gel data image coordinate grid.

The quality of the tracking result can be scored by comparing the expected grid locations with the observed data peak locations—straight data grids indicate a high quality result, whereas large distortions indicate a lower quality result. One useful quality score measures the curvature of the observed peaks by forming the sum of local neighbor distances, and normalizing relative to the nieghbor distances in a straight idealized grid. This grid is preferably formed from the known lane loading pattern, the known size standard positions, and observed grid data (e.g., mean boundary positions).

With two dimensional gel image data f(x,y,z), z denoting the color plane, there also is the step of extracting lane profiles from the gel image to form a set of one dimensional profiles. The lane tracking result is used in this step. For each lane, form the mapping from y-pixel values to the (x,y) pixel locations indicated by the size standard location found for the lane. Create a spline function (e.g., cubic) that interpolates through the mapped v:y→x pixel pairs to all other (x,y) pixel values. Then, extract a one dimensional profile (for each color k), where the domain values down the lane are the desired sequential pixels y, and the range values are computed from the function f(v(x),y,z). This procedure is done for each data image plane z, extracting either color separated data (by applying the correction matrix) or unseparated data. Referring to FIG. 1, Step 6 is for extracting the profiles.

The signal profile of a capillary or lane is $f(x_{pixel},z)$, where z denotes the label color (or channel). This function is available for capillary data available after processing Step 2, and for gel data after extracting profiles in Step 5.

The pixel sampling of the electrophoresis distorts the sizing of the raw data. The size tracking result from Step 5 provides as set of $(x_{pixel},x_{size})$ pairs. Use these matched pairs to form the coordinate transformation $\mu: x_{pixel} \to x_{size}$. Combining the functions f and $\mu$ via a double interpolation to form:

$$f \circ \mu^{-1}(x_{size}, z),$$

a new function that describes the signal as a function of size standard units (instead of pixel units), preferably in base pair size units. If color separation has not yet been done, the correction matrix is applied at this time. These transformed (capillary or gel data) profiles are then preferably stored in an n×k data structure of sized profiles, where n is the number of pixel samples, and k is the number of dye colors.

Note that the $f_{pixel} \circ \mu^{-1}(x_{size}, z)$ transformation which maps $$x_{size} \to f_{size}(x_{size})$$

can be usefully understood as the commutative diagram:

$$\begin{array}{ccc} x_{size} & \xrightarrow{f_{size}} & f_{size}(x_{size}) \\ \downarrow \mu^{-1} & & \uparrow identity \\ x_{pixel} & \xrightarrow{f_{pixel}} & f_{pixel}(x_{pixel}) \end{array}$$

The transformation is preferably implemented by performing a double interpolation. In MATLAB, this operation can be readily computed using the 'interp1' function where:

YI=interp1(X,Y,XI, method)

interpolates to find YI, the interpolated values of the underlying function Y at the points in the vector XI; the vector X specifies the points at which the data Y is given.

With 'interp1', interpolate the desired size domain points into computed pixels using the monotonic bijection between expected sizes and observed peak pixels:

pixels=interp1(sizes, peaks, domain, 'spline')

Cubic spline interpolation is done by setting the method to 'spline'. Then, interpolate the function f on the desired size domain points (i.e., the computed pixels) using the monotonic bijection f(i) between indices {i} and data values f{i}:

indices=[1:length(data)];

profile=interp1(indices, data, pixels, 'spline');

Computing profile completes the commutative diagram, and produces the new function $f_{size}(x_{size})$.

Referring to FIG. 4, visualizations are shown for the results of processing Steps 1–6.

The computer software preferably extracts and analyzes data automatically, without human intervention (if so desired). The software separates colors using a matrix, which is either precalibrated or created from the data, depending on which module is used. The software tracks lanes and size standards on two-dimensional gel data automatically by mapping the expected two dimensional lane/size grid to the observed size standard data; on one-dimensional CE data, size tracking is done separately for each capillary. The user interface software makes manual retracking, zooming, and single-click access to the chemistry panel (or sample data used on a run) available to the user throughout.

A chain of custody is maintained in that the user preferably cannot move to the next step without saving results (manually or automatically) from the current step. Changes are saved, not discarded; moreover, the software records these changes incrementally, so that the audit trail cannot be lost by early program termination.

Backtracking capability and flexibility are preferably included in the software. For example, should fully automated lane tracking fail due to low-quality data, the user can choose to: (a) edit the results, and have the program re-track, (b) edit the results without re-tracking, (c) manually track the lanes and sizes, or (d) reject the low-quality gel. A "revert" operation provides a universal Undo operation for automatically rolling back major processing steps.

Data Scoring

Figures 5, 6:
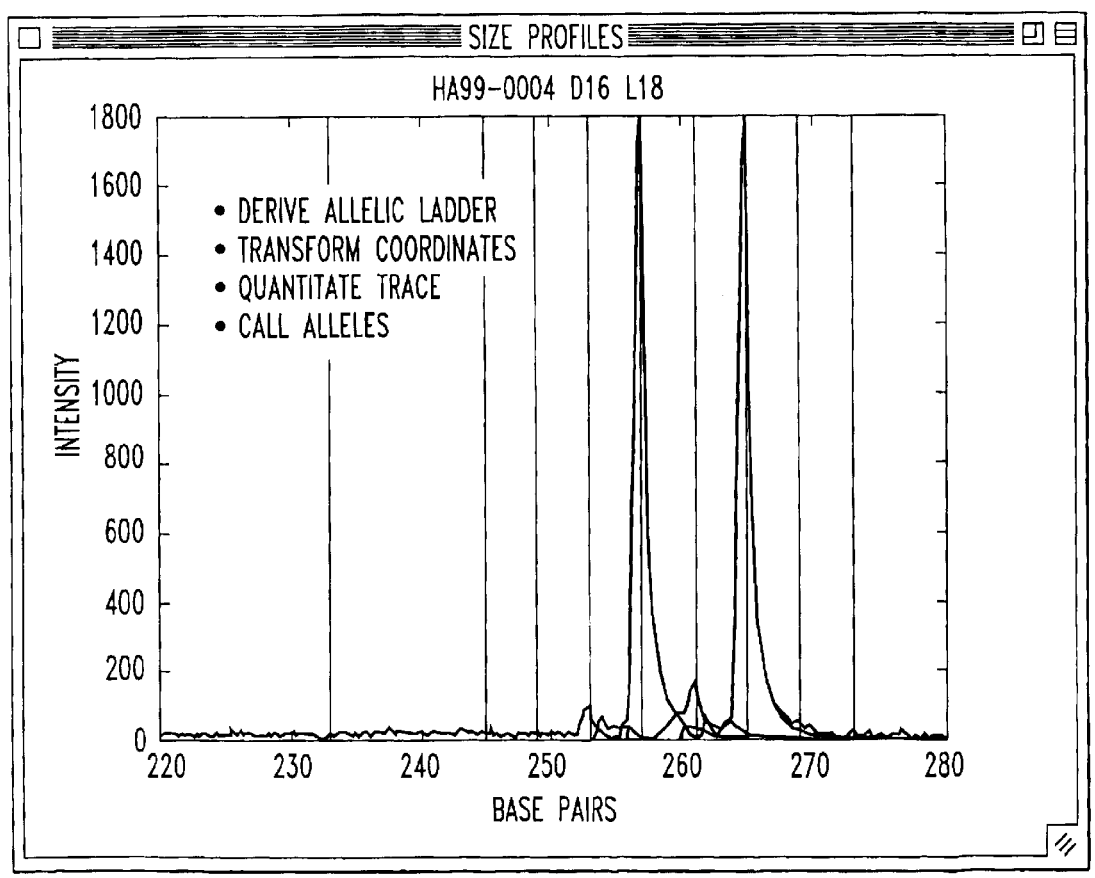
FIG. 5 shows the steps of quantitating and analyzing genetic data.
FIG. 6 shows the results of ladder processing, peak quantitation and allele calling.

Referring to FIG. 5, Step 7 is for deriving an allelic ladder.

It is useful to have a set of reference peaks that (a) correspond to the actual locations of DNA molecules on the gel, (b) have known lengths (in base pair units), and (c) cover a large part of the sizing window. This reference set can be developed for any fragment sizing genetic assay; without loss of generality, the preferred embodiment is described for STR genotyping.

Construct a partial allelic ladder by PCR amplifying a pool of DNA samples. This allelic ladder, and optionally a known sample, are preferably loaded into the electrophoretic system as separate signals (i.e., in different lanes or colors). After the gel is run, referring to FIG. 1, Steps 1–6 are performed to initially process the signals. Then, preferably in size coordinates (rather than in pixel coordinates), a peak finding algorithm locates and sizes the peaks in these two lanes with respect their in-lane size standards. The known sample's sized peaks are then compared with the similarly sized peaks found in the ladder lane. Following this comparison, the known DNA lengths are then assigned to the allelic ladder. The DNA length labels of these DNA lengths are then propagated to the unlabeled ladder peaks.

A preferred peak labeling procedure is:

1. In the ladder signal, find the domain positions (i.e., the sizes relative to the size standards) of the allelic peaks.

2. Perform a relational labeling from the known signal to the allelic ladder signal, as follows. Find the peaks of the known signal, and assign to them their known sizes (in allelic sizes units, such as base pairs). Then, match (in size standard units) these known allele peaks to the peaks in the ladder signal having corresponding size. Designate these ladder peaks with the allelic size labels of the known peaks.

3. Extend these allelic label assignments from the allelic ladder peaks designated with known labels to the rest of the ladder peaks.

3a. When the expected size pattern of the alleles on the allelic ladder is known (as with previously characterized forensic ladders), a robust method for assigning size labels to data peaks uses a standard open/closed search set artificial intelligence (AI) algorithm. Start from the most confident data (i.e., the knowns) as the closed set, with all remaining peaks in the open set. Each cycle, (i) select an open ladder allele that is nearest in allele size to a closed ladder allele, (ii) predict the calibrated size (from the size standards) of this allele using interpolation relative to the closed peaks, (iii) find the allelic ladder peak whose calibrated size is closest to the predicted size in (ii), and (iv) if the quality score (based on size deviation) is good enough, move this candidate open peak to the closed set. On termination, only the most confident ladder peaks in the observed data have been matched to expected ladder alleles. See (N J Nilsson, Principles of Artificial Intelligence. Palo Alto, Calif.: Tioga Publishing Co., 1980), incorporated by reference.

3b. When expected ladder alleles are not available (e.g., with uncharacterized pooled DNA samples), the ladder pattern alone (peak spacing or peak heights) usually contains sufficient information for designating the labeling. Start with the most confident data—known allele peaks, or tallest ladder peaks. Then, locally extend the allele labels to the size peaks. Since there is more uncertainty without a known ladder pattern, more search is useful. One preferred method is to (i) find the tallest (most confident) peak, (ii) match size with nearest (bp size) allele, (iii) locally align iteratively for smaller and larger peaks, (iv) assign a quality score to the alignment, (v) repeat the preceding three steps, but shifted one or two sizes up or down, and (vi) select the alignment with the highest quality score.

4. Optionally, fill in any missing ladder peaks with interpolation by reference to past ladder data.

5. Fill in the virtual points on the ladder. These are expected ladder alleles that are believed to exist in the population, but that are not represented as peaks in the allelic ladder. This is done by interpolation.

6. Return the results assigning allele labels (e.g., in base pair or other integer units) to data ladder peaks (e.g., in size standard units). It is preferable to report the quality score of the assignment.

In nonforensic STR applications, where previously characterized ladders are generally unavailable, pooled alleles of a given marker can be used as a reference ladder. This novel approach can help eliminate the size binning problem that plagues microsatellite and other STR genetic methods. It is preferable to use the same allelic ladder across multiple runs. The ladder can be comprised of either pooled DNAs that are PCR amplified together, or post-PCR amplified products that are then pooled together. It may be desirable to visually inspect the ladders. In one preferred embodiment, previously uncharacterized ladders are checked the first time that they are encountered, with a human editor identifying the best peaks to use and matching them against their expected sizes. Recording quantitative peak data for a ladder can enable the use of quantitative computer-based matching of reference ladders and new unknown ladders (e.g., for peak and size alignment) by correlation or other inner product methods.

When the interpolation and extrapolation have finished, the allele sizes that were actually present as peaks in the ladder data, as well as desired allele sizes that were not present as peaks, have all been allocated to size positions.

SNP ladders can be developed in a similar way to STR ladders. With multiplexed SNPs, it is useful to run allelic sizing ladders comprised of actual SNP data for the markers of interest in a signal. Then, comparison of the unknown SNP sample data with the SNP allelic ladder can remove uncertainty regarding the correct size (hence, allele) assignment. The same reasoning applies to any size-based assay for which a (partial or complete) ladder of candidate solutions can be developed.

With gel electrophoresis, it is preferable to include on the gel at least one allelic ladder for every marker used. For example, one lane can be dedicated to ladders for the marker panel used in the other lanes; this lane can be loaded in duplicate on the gel. It is also desirable to include at least one known reference allele lane on every gel; this signal can be one or more positive PCR controls. The advantage of duplicate control lanes (for ladders and reference controls) is that when there is a PCR, loading, detection, or other failure in one lane, the signal in the other lane can be used. Moreover, a comparison of the two (or more) signals can suggest when such a failure may have occurred.

With capillary electrophoresis, it is similarly preferable to use ladder and reference controls.

With single capillary systems (such as the ABI/310), these controls should be run at some point during the lifefime of the capillary. Preferably, the controls should be run as often as the temporal variation in the sizing system (i.e., differential sample and size standard migration) warrant.

With a multiple capillary instrument (e.g., ABI/3700, MegaBACE, etc.) each capillary can form its own electrophoretic separation system. In the most preferred embodiment, the allelic ladder, known reference samples, and any other capillary controls (for fragment sizing, color separation, etc.) are run at least once for every capillary, with the calibration results then applied specifically to that capillary. For example, consider the case of using one panel comprised of a set of markers, with this panel applied to a set of s samples, run out on an n-capillary instrument that achieves r sequential runs per capillary with acceptable sizing fidedility. Suppose (for high-throughput studies) that, approximately, $n \times r \leq s$. Then, one of the runs (e.g., run number 1 or r/2) should have allelic ladders in all n capillaries, and another run (e.g., run number 2 or 1+r/2) should have allele references in all n capillaries.

Generating data containing these allelic ladder sizing controls, and analyzing the data as described in this step, reduce run-to-run sizing variation. Such reduction in gels or capillaries is crucial for achieving reproducible sizing assays. Variable run conditions (e.g., temperature, gel consistency, formamide concentration, sample purity, concentration, capillary length, gel thickness, etc.) can induce differential sizing between the PCR products in the sample and the internal size standards. These allelic ladder comparison methods help correct for such variation.

Referring to FIG. 5, Step 8 is for transforming coordinates.

In the preferred embodiment, size comparisons used in the analysis are performed in the allelic ladder size coordinate system, rather than in the size standard coordinate system. While the latter approach is also workable, the former method has the advantages that the reference system is comprised of DNA bands size calibrated to actual integer DNA molecule lengths, rather than to artibrary fractional molecular weight sizing units. Using integer DNA lengths (e.g., true base pairs) is closer to the physical reality, and can simplify the data analysis, logical inference, communication with the user, quality assurance, and error checking.

In one preferred embodiment, the signals are kept in size standard units, but comparisons are made in the allelic ladder frame of reference. For example, in comparing sample peaks with allelic ladder reference peaks, the sample peaks can first be interpolated into a domain based on the allelic ladder peak sizes, prior to comparing the sample peaks with any other reference sizes.

A ladder-based peak sizing method can establish a direct connection between observed peak sizes and actual DNA fragment lengths (possibly up to a constant shift). Transforming data sizes into DNA lengths overcomes size binning problems. For example, rounding number to the nearest integer in DNA length (i.e., ladder) coordinates permits the assigning of consistent labels to each peak; this consistency is not achieved when round fractional peak size estimates. Moreover, the peak's deviation from the integer ladder provides a quality measure for how consistently the peaks are sizing on a particular size separation run.

In the most preferred embodiment, the sample signals are transformed from size standard units into allelic ladder DNA length units. Step 6 provides the sized signal profile of a lane (or capillary):

$$f \circ \mu^{-1}(x_{size}).$$

Step 7 provides a characterized allelic ladder that matches the alleles of the ladder in size standard units with corresponding DNA molecule lengths in base pairs (or other suitable integer-spaced units). This pairing defines a coordinate transformation for that ladder:

$$\lambda: x_{size} \to x_{length}.$$

Combining the function $f \circ \mu^{-1}$ together with the function $\lambda$ (this can be done using a double interpolation) forms:

$$f \circ \mu^{-1} \circ \lambda^{-1}(x_{length}),$$

which represents the signal intensity f in terms of DNA length $x_{length}$. The relevant mathematics and computer implementations are detailed above in Step 6, extracting the profiles. For each marker, with n lanes or capillaries, and k colors, these transformed profiles can be preferably stored in an n×k data structure (e.g., in memory, or in a file).

This procedure provides a method for analyzing a nucleic acid sample. The steps included: (a) forming labeled DNA sample fragments from a nucleic acid sample; (b) size separating and detecting said sample fragments to form a sample signal; (c) forming labeled DNA ladder fragments corresponding to molecular lengths; (d) size separating and detecting said ladder fragments to form a ladder signal; (e) transforming the sample signal into length coordinates using the ladder signal; which in turn permit (f) analyzing the nucleic acid sample signal in length coordinates, as follows.

Referring to FIG. 5, Step 9 is for quantitating signal peaks.

In addition to sizing DNA peaks, it is also useful to quantitate the relative amount of DNA present. To do this accurately requires taking account of band overlap. Few systems currently perform this band overlap analysis; those that do (e.g., Cybergenetics' TrueAllele software), use a combinatorial approach that increases analysis time greatly as the number of adjacent peaks increases. This combinatorial cost can impede analyses of large allelic ladders or of differential display data. In the preferred embodiment, as described herein, the DNA quantitation step for resolving band overlap should computationally scale (e.g., at linear or small polynomial cost) with the number of bands analyzed.

In DNA length coordinates, as developed in Step 8, a peak has a natural shape that stems from band broadening as it migrates down the gel or capillary. (For accurate peak quantitation, DNA length coordinates are preferrable to size standard coordinates, and size standard coordinates are preferrable to pixel scan coordinates.) Centered at location $x_k$, this peak shape can be described as a Normal function $$\phi_k^L(x) \propto e^{-\frac{1}{2}\left(\frac{x-x_k}{\sigma}\right)^2}$$

on the leading edge, and a Cauchy function $$\phi_k^R(x) \propto \frac{1}{1+\left(\frac{x-x_k}{\alpha}\right)^2}$$

on the receding edge; the functions share the same height h at $x_k$. Band broadening implies that as $x_k$ increases, the width parameters $\sigma$ and $\alpha$ will increase, the height h will decrease, while the area remains constant. This is confirmed by fitting peak spread data as a function of DNA length with a third order exponential function.

Using the changing band shapes as a set of basis functions, write the trace f (in DNA length coordinates) as:

$$f(x) = \sum_{k=1}^{n} c_k \cdot \phi_k(x)$$

where basis function $\phi_k$ depends on $<x_k, \sigma_k, \alpha_k, h_k>$, i.e., the center position $x_k$, Normal spread $\sigma_k$, Cauchy spread $\alpha_k$, and center height $h_k$.

From the data f(x), solving for the coefficients $\{c_k\}$ provides an estimate of the DNA concentration at each peak. Less efficient approaches (e.g., TrueAllele) currently solve this equation by a least-squares search of the 4n coefficients to the data f, with combinatorial computing time proportional to exp(4n). However, by exploiting the model functions $\phi_k$, together with function space mathematics, this computing time can be reduced to roughly linear cost, proportional to n. See (F Riesz and B Sz.-Nagy, Functional Analysis. New York: Frederick Ungar Publishing at Co., 1952), incorporated by reference.

Normalize the basis functions $\phi_k$ so that $$<\phi_k(x), \phi_j(x)> = 1$$

and note that the band overlap coefficients $b_{k,j}$ can be numerically estimated from the model functions as $$<\phi_k(x), \phi_j(x)> = b_{k,j}$$

Then observe that with initial estimates of $x_k$ (assuming one peak per bp size k), rewrite the inner product $<f, \phi_j>$ as:

$$\langle f, \phi_j \rangle = \left(\sum_{k=1}^{n} c_k \cdot \phi_k\right) \cdot \phi_j = \sum_{k=1}^{n} c_k \cdot (\phi_k \cdot \phi_j) = \sum_{k=1}^{n} c_k \cdot b_{k,j}$$

Setting the data derived values $\{d_j=<f, \phi_j>\}$, and using appropriate vector-matrix notation, yields the relation:

$$d = c \times B$$

With sparse peak data that has little band overlap (e.g., tetranucleotide repeat data) $B=I_n$ (the identity matrix), and $c \approx d$ immediately yields the DNA concentrations at every peak k. More generally, B is largely an identity matrix (i.e., primarily zeros off-diagonal), but has a few small near-diagonal elements (the band overlaps) added in. Solve for c from the observed data vector d and the band overlap matrix B using a very fast matrix inversion algorithm (e.g., SVD) that exploits the sparse nature of the local overlap coefficients.

In the most preferred embodiment, the overlap matrix B is used to rapidly estimate the DNA concentrations $\{c_k\}$ at the peaks. This is done by computationally exploiting the functional analysis. Since $$d = c \times B,$$

rewriting yields:

$$d \times B^{-1} = c \times B \times (\times B^{-1}) = c$$

or $$c = d \times B^{-1};$$

and so the DNA concentrations c can be estimated immediately from the values $\{d_j = <f, \phi_j>\}$ derived from data signal f once the $\phi_j$ and their overlap integrals $B = <\phi_j, \phi_k>$ are known.

In the preferred embodiment, estimate the $\phi_j$ basis functions and their overlaps. Each basis function $\phi_k$ depends on $<x_k, \sigma_k, \alpha_k, h_k>$. To reduce this four dimensional search to one dimension, proceed as follows.

$x_k$ can be estimated from the peak center.

$h_k$ is not a factor, since each $\phi_k$ is normalized to integrate to 1.

$\sigma_k$ and $\alpha_k$ are empirically observed to be in a fixed ratio to one another (at least in local neighborhoods), due to the relatively constant peak shapes.

Therefore, a computationally efficient approach is to perform a one dimensional search for $\sigma_k$ and $\alpha_k$, keeping their ratio fixed. Then, if so desired, perform a quick local two dimensional search to in the solution neighborhood to refine the values of $\sigma_k$ and $\alpha_k$.

To find the peak width parameters $\sigma_k$ and $\alpha_k$, first fix a value of $\sigma$ in a local neighborhood; in 1D search, set $\alpha$ to a fixed r proportion of $\sigma$; in 2D search, set the value of $\alpha$ as well. For each observed peak, set the center $x_k$ of $\phi_k$ to the peak's center location. Following normalization, the basis functions $\{\phi_k\}$ are determined. Then, for j's in the neighborhood, compute $d_j=<f, \phi_j>$, or:

$$d = <f, \phi>$$

Determine B by numerical (or closed form) integration of the basis functions $\phi_j$ and $\phi_k$:

$$B = [\langle \phi_k, \phi_j \rangle]$$

Compute $B^{-1}$ by inverting B, or:

$$B^{-1} = [\langle \phi_k, \phi_j \rangle]^{-1}$$

Note that terms far from the diagonal are essentially zero. These local neighborhood calculations of d and $B^{-1}$ are rapid, and are used in the inner loop of the following minimization procedure.

Minimize the difference between the observed data signal f and the expected model function:

$$f(x) - \sum_{k=1}^{n} c_k \cdot \phi_k(x - x_k)$$

by substituting the $c_k$ computed from:

$$c = d \times B^{-1}$$

Minimization (e.g., using an $L_2$ norm) of the expression:

$$\left\| f(x) - \sum_{k=1}^{n} (d \times B^{-1})_k \cdot \phi_k(x - x_k) \right\|_2$$

in the neighborhood as σ (and possibly α) vary, finds the best estimate of the widths of the basis function. These widths can be modeled locally, interpolated by fitting with a cubic exponential function, and then used to generate appropriate basis functions across the full range of sizes.

Application of these modeled basis functions to the data function f produces robust estimates of the DNA concentration $c_k$ at each DNA peak k, since, after convergence, $$c = d \times B^{-1}.$$

In the current art, workers use the heights or areas of the data peaks. Because-of the extensive peak shape modeling done here, it is preferrable to use the heights (i.e., $c_k$) or areas (determined from $c_k$ and the $\phi_k$ peak shape, e.g., by closed form evaluation) of the computationally modeled peaks.

The match-based quantitation described herein is very well suited to highly multiplexed data, such as SNPs, differential display, DNA arrays, and pooled samples. This is because the inner product operations (and local band overlap corrections) can be applied accurately and in constant time, regardless of the number of data peaks in the signal.

It is useful to assess the quality of the individual peak quantitation results. This assessment can be done by comparing the modeled data function $$\hat{f}(x) = \sum_{k=1}^{n} c_k \cdot \phi_k(x)$$

with the observed data signal f. A normalized $L_2$ deviation (computed, e.g., via a correlation) between expected and observed based on the minimization search function above can be used as the comparison measure.

Referring to FIG. 5, Step 10 is for analyzing the data, preferably by calling the alleles.

In the preferred embodiment, allelic (or other) DNA ladder data is available, and the alleles can be called by matching sample peaks relative to the ladder peaks. This match operation is fast, reliable, very accurate, and accounts for inter-gel or inter-capillary variations. Depending on the application, a window (typically ±0.5 bp) is set around a ladder peak of calibrated DNA length. When a sample peak (preferably in ladder coordinates) lies within this bp size window, it can be reliably designated as having the length of that ladder peak. Zero size deviation between the centers of sample and ladder peaks indicates a perfect match; greater deviations indicate a less reliable match.

In an alternative preferred embodiment, the data profiles can be stored in size coordinates, and brought into length coordinates only when needed. This is done by retrieving a sample's size coordinate profile, as well as and the ladder peaks. The sample's peaks are found in size coordinates, and then interpolated in into length coordinates using the ladder size to peak mapping, as described previously. The sample's peaks are then in length coordinates, and can be rounded to the nearest integer, or matched against integers representing valid allele designations. The deviation from such integers (e.g., the fractional component) can be used a measure of quality, accuracy, or concern.

In other embodiments, found in the current art's fragment sizing software, the peak sizes (e.g., the alleles in genotyping applications) are analyzed in a size standard coordinate system, and ladder calibration data is not used by the computer. This analysis entails a bottom-up collection and comparison of data from many samples to form data-directed bins. These bin distributions are then used to designate sample peak size. However, the distribution variance across multiple electrophoresis runs on different samples can be quite high. When these bins have overlapping sizes, allele size designation becomes quite uncertain.

In the preferred embodiment, both DNA length and amount are used in scoring the data. With STR genotyping, for example, where there can be multiple peaks, the DNA concentration (e.g., modeled peak height or area) is used as measure of confidence in the observed peak. With a heterozygote genotype, two peaks are expected, and with a homozygote, only one. Since other peaks may be present from mixtures, PCR artifacts, or other DNA sources, the analysis will focus on the higher concentration peaks, particularly those peaks residing in allelic ladder windows. Most of the peak signal mass should be concentrated in the most confident peaks: high DNA amount, and in a ladder window. When this is not the case, confidence in the data is lower. Once the peaks have been quantitated at known DNA lengths, the data can be further analyzed. Such analyses include stutter deconvolution, relative amplification correction, allele calling, allele frequency determination (from pooled samples), differential display comparisons, and mutation detection. In genotyping applications, allele calling should be done on the signals only after corrections (e.g., for stutter or relative amplification) have been made. See (M W Perlin, "Method and system for genotyping," U.S. Pat. No. 5,541,067, Jul. 30, 1996; M W Perlin, "Method and system for genotyping," U.S. Pat. No. 5,580,728, Dec. 3, 1996; S-K Ng, "Automating computational molecular genetics:

solving the microsatellite genotyping problem," Carnegie Mellon University, Doctoral dissertation CMU-CS-98-105, Jan. 23, 1998), incorporated by reference.

In one preferred embodiment, allele calling on quantitated corrected data is done by:

1. Finding the largest peak (area or height), and ensuring that is within a window on the allelic ladder.
2. Removing all peaks from the signal that either (a) have a DNA length that is not in a window of the allelic ladder, or (b) have a DNA amount that is not within some minimum percentage of the largest peak.
3. Calling the alleles by matching the DNA lengths of each sample peak to the DNA sizing windows on the allelic ladder.
4. Applying rules to check for possible data artifacts. Typical rules are described below.
5. Computing a quality score, particularly for those data apparently free of data artifacts. Various quality score components are discussed below.
6. Recording the designated alleles, and the quality of the result.

Referring to FIG. 6, the results of ladder processing, peak quantitation and allele calling can be visualized.

There are many "junk-detecting" rules that can be designed and applied to data. Critical to all such rules is the ability to compare observed measures against expected behaviors. By modeling the steps of the processing, computing appropriate quality scores at each step, and comparing these observed data features with normative results, the invention enables a precise computer diagnosis of problems with data signals and their quality. Some example rules include:

Noise only. Using measures (such as Wilcoxon's signed-rank statistic) to test for randomness, a computer program can decide that an experiment produced primarily noise (B W Lindgren, Statistical Theory, Fourth Edition. New York, N.Y.: Chapman & Hall, 1993), incorporated by reference.

Low signal. The peaks should have heights over a certain (user-defined) minimum threshold. When a profile's highest peak does not reach that threshold, flag the problem.

High signal. The peaks should not be over a certain (user-defined) maximum threshold. When a profile's highest peak does exceeds that threshold, flag the problem.

Peak dispersion. The designated peaks should comprise a certain percentage of the total signal. If a profile's designated peaks contain less than that percentage, fire the rule.

Algorithm conflict. When multiple scoring algorithms are used, they should agree on the scoring results. Report any conflicts.

Relative height. For some applications (e.g., forensic STR analysis) the relative peak heights should be within a predefined ratio of each other. Indicate when a genotype has a second peak with a relative height that is too low.

Third peak. One (homozygote) or two peaks (heterozygote) should contain most of the DNA signal. Indicate when a genotype has a third peak that contains too much DNA signal.

Off ladder. All the allele peaks should be close to their ladder peaks. When one (or more) of the alleles are too far away from their ladder peak, inform the user.

Uncorrelated. When there are two allele peaks, their centers should deviate similarly from their respective ladder peaks. When a genotype has deviations that do not correlate (i.e., their difference exceeds some threshold), flag the problem.

Control check. The calls computed for a control experiment should be consistent with the known results. When they are not, flag the result.

Note that some of these rules (e.g., "off-ladder") make use of allelic ladders, when they are present.

To better understand the decision support role of each numerical quality score (such as those used in rules), and their decision thresholds, it is useful to collect the scores for a large set of data and analyze them. Collection proceeds by recording the set of scores for each applicable genotype result, and indexing the genotypes (say, by sample, gel, and locus). Consider each such numerical score as a mapping from the genotypes to $\Re^1$. Classify the genotypes by how they were scored; one preferred classification includes unscorable (e.g., noise), low quality (e.g., rule firings), correctly called good data (e.g., human agreement), and incorrectly called good data (e.g., human agreement). The result classification can be obtained by comparing the computer calls (and rule firings) with human edited (or otherwise independently scored) data. On some useful subset of genotypes (e.g., each locus examined separately), the numerical quality scores can be collated and histogrammed for each result classification; this produces a set of distributions, one for each classification. Comparing (numerically, visually, statistically, etc.) the different distribution profiles for the different classifications provides insight into the utility and scaling of a numerical quality score, permitting the derivation of decision thresholds or probability models. In a preferred embodiment, a decision threshold is statistically determined by distinguishing two score distributions (e.g., correct and incorrect results) according to a determined sensitivity or specificity. In another preferred embodiment, linear or logistic regression is used to model the probability of an accurate allele call. These thresholds or probabilities can be displayed to a user for enhanced confidence or decision support.

It is useful to compute a quality score on the good data; one criterion for "good data" is that the experiment does not trigger any "junk" detecting rules. Quality scores enable the ranking of experiment results for selective review, as well as the computation of accuracy probabilities. Many possible quality scores can be developed, depending on the application and the available data. In all cases, there is some kind of comparison between expected behavior and an observed result—small deviations indicate high quality, whereas large deviations suggest lower quality. Example quality scores include:

Domain measures. When ladder data is present, it is possible to compute the deviation between a candidate allele peak center and its associated ladder peak center. When ladder data is not present, a similar comparison can be made relative to a precalibrated bin center, rather than a ladder peak center. One useful score is the maximum (over the scored alleles) of the absolute value of the deviations. When this number is close to zero, the confidence is high. As it increases to 0.5 bp, the result becomes less confident.

Range measures. A sizing data result pertains to an particular number of peaks; any additional peaks represent a dispersion of the signal mass away from the hypothesized score. Ideally, all the signal mass should be present in the called peaks, which can be measured by the peak centering ratio=(called peaks)/(all peaks). When this ratio is near unity, the confidence is high. As it decreases to zero, the result becomes less confident.

Product measures. A product of a domain measure with a range measure can be a sensitive indicator of quality. In one preferred embodiment, let a result scale with 1 as the highest quality, and 0 as the lowest quality. Rescale the domain measure above to map the score interval [0,0.5] to the quality interval [1,0], with all scores above 0.5 set to 0. Rescale the range measure above to map the score interval [0,1] to the quality interval [1,0]. Then form the product of these two rescaled scores, so that the result lies in the interval [0,1].

Function measures. Once all data corrections have been made (e.g., for PCR stutter, relative amplification, peak shapes, peak sizes, peak center deviations, band overlap, etc.) on the fully quantitated and modeled signal, the inverse of these corrections can be applied to the size result to resynthesize the signal. Comparison of the resynthesized signal with the data signal provides a measure of how completely the analysis modeled the data—the residual deviation can measure lack of confidence in the result. One such comparison is a correlation between the synthesized and data signals. This correlation can be computed so that small values indicate confidence (e.g., using a normalized $L_2$ deviation), or so that larger values indicate confidence (e.g., using a normalized inner product or statistical correlation measure).

The development of some quality scores has been described (M W Perlin, "Method and system for genotyping," U.S. Pat. No. 5,876,933, Mar. 2, 1999; S-K Ng, "Automating computational molecular genetics: solving the microsatellite genotyping problem," Carnegie Mellon University, Doctoral dissertation CMU-CS-98-105, Jan. 23, 1998; B Pálsson, F P álsson, M Perlin, H Gubjartsson, K Stefánsson, and J Gulcher, "Using quality measures to facilitate allele calling in high-throughput genotyping," Genome Research, vol. 9, no. 10, pp. 1002–1012, 1999), incorporated by reference.

Probabilities can be computed from quality scores. The individual components of the quality scores generally lie on a numerical scale. Histogramming and multivariate regression analysis can provide insight into the distribution of the correctly scored "success" data population relative to the distribution of the incorrectly scored "failure" data population along each of these measures. A logit transformation of this dichotomous outcome variable is useful, and provides [0,1] bounds for probability estimates, and the use of a binomial (rather than normal) distribution for the error analysis. By applying standard logistic regression, the key underlying independent variables can be elucidated. This logistic regression analysis can help determine the thresholds used in the "junk-detection" rules, and, for each experiment, can compute the probability of an accurate score from the observed variables. For example, the domain and range measures used above can be used as two independent variables, with the outcome being success or failure in the computer correctly calling the allele results. Logistic regression on these variables with a preanalyzed data set can be used to construct a correctness probability for allele calls on further data sets. See (A Agresti, Categorical Data Analysis. New York, N.Y.: John Wiley & Sons, 1990; D W Hosmer and S Lemeshow, Applied Logistic Regression. New York: John Wiley & Sons, 1989; Statistical Analysis Software, SAS Institute, Cary, N.C.; Statistical Package for the Social Sciences, SPSS Inc., Chicago, Ill.), incorporated by reference.

Data Review

Once the automated computer scoring has completed, it is often useful to have a person assess the results. Since reviewing perfectly scored data is an inessential step, the data review should optimally focus on reviewing the least confident (but scorable) data. The outcome of this focused review is typically a decision for each experiment's result: accept the result, modify the result, reject the result, plan to redo the experiment in the laboratory, and so on.

In order to focus the data review, it is helpful to have a prioritization. In the preferred embodiment, the quality score or accuracy probability is used to rank the experiments. The review may arrange the suspect experiments in different subsets, e.g., grouped by marker, sample, equipment, personnel, time, location, etc. By reviewing the worst data first (i.e., rule firings, least quality scores), the user is enabled to focus on evaluation and repair of only the suspect data. Not reviewing highly confident data frees up human operator time for other process tasks. Moreover, not reviewing unscorable data is similarly useful.

Using these methods, low quality data can be identified and classified. At the single datum level, individual results can be examined and better understood. At the data set level, problematic loci, samples or runs can be identified by examining percentages of outcome indicators (e.g., rule firings, low quality scores, calling errors) relative to data stratifications. For example, the number of miscalls of known samples (arranged by locus and gel run) can identify problematic data trends early on. This information can provide useful quality control feedback to the laboratory, which can help improve the overall quality of future data generation.

Figure 7:
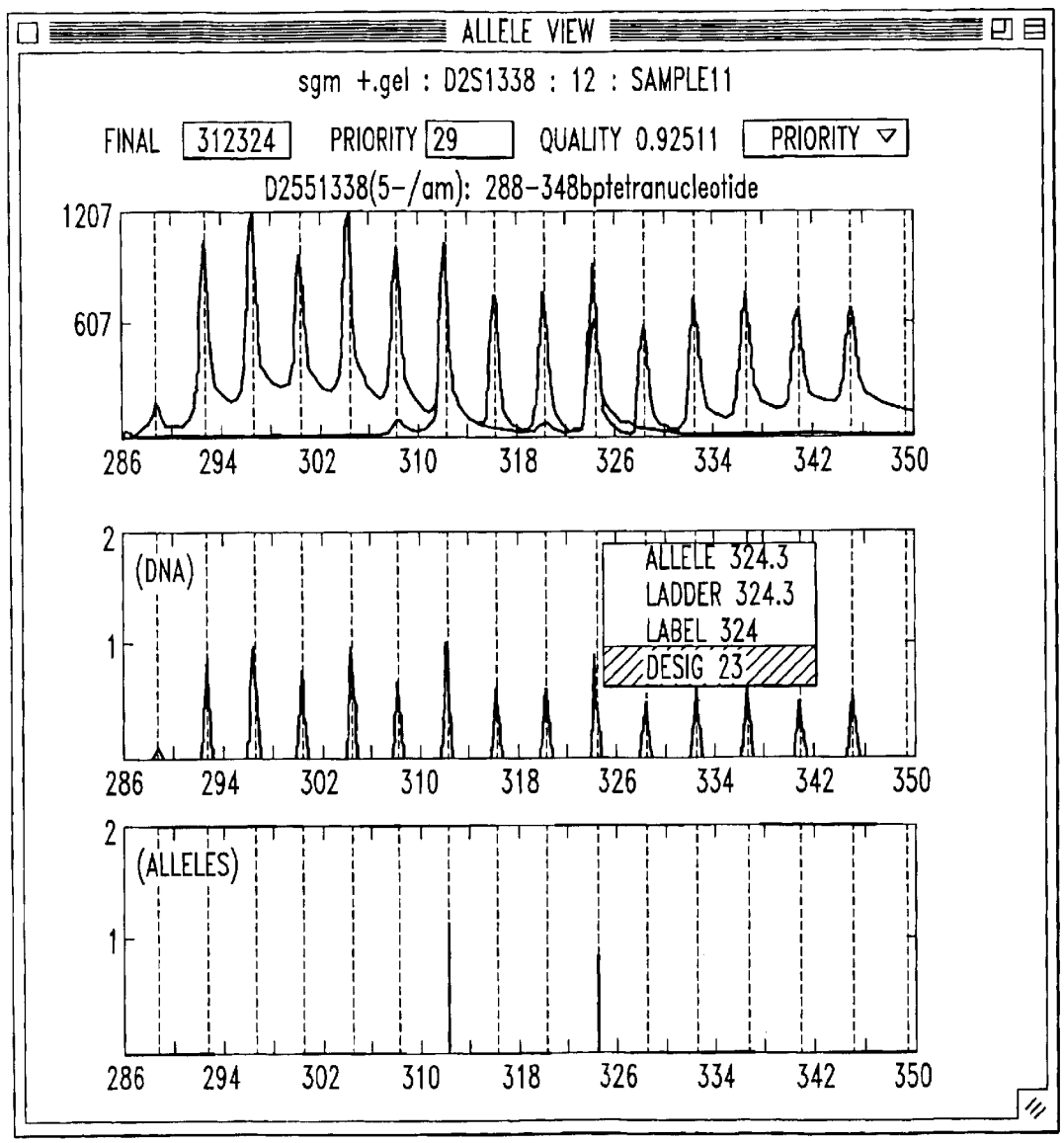
FIG. 7 shows a graphical user interface for navigating prioritized genotyping results.

Referring to FIG. 7, it is useful to present the results graphically. Visualizations of the experiments (e.g., gel lane tracking or color separation) and the signal traces help the user understand potential problems with the data, and possibilities for their correction (both for the particular experiment, as well as for the overal data generation process). In the preferred embodiment, multiple graphical visualizations for inspecting and reviewing genotype data include interfaces for:

inspecting and annotating the raw gel data;
  inspecting and editing the automated lane tracking and sizing;
  assessing data quality and marker size windows;
  reviewing and editing automatically called alleles (by quality score priority, or other user-selected data rankings), preferably with all data and inferences visually presented in the context of the marker's allelic ladder;
  visually examining the data signal, preferably overlaid upon an allelic ladder;
  flexible examination of bleedthrough (or "pull-up") artifact;
  reviewing computed DNA quantitations and sizes, preferably in the context of the allelic ladder. A more detailed window explores the quantitation results.
  showing the allele calls;
  providing access to a more detailed textual window presenting a summary of useful allele calling information in tabular form;
  focusing on the allelic ladder data signals, when available; and
  displaying selected multiple lane signals graphically in one view.

Such multiple representations visually show the quality of the data, and provide diverse, focused insights into the data and their processing. Such graphical interfaces are generally used on only a small fraction (e.g., less than 5%–10%) of the data, since most high-throughput users do not care to revisit high-quality allele calls on high-quality data.

Figure 8:
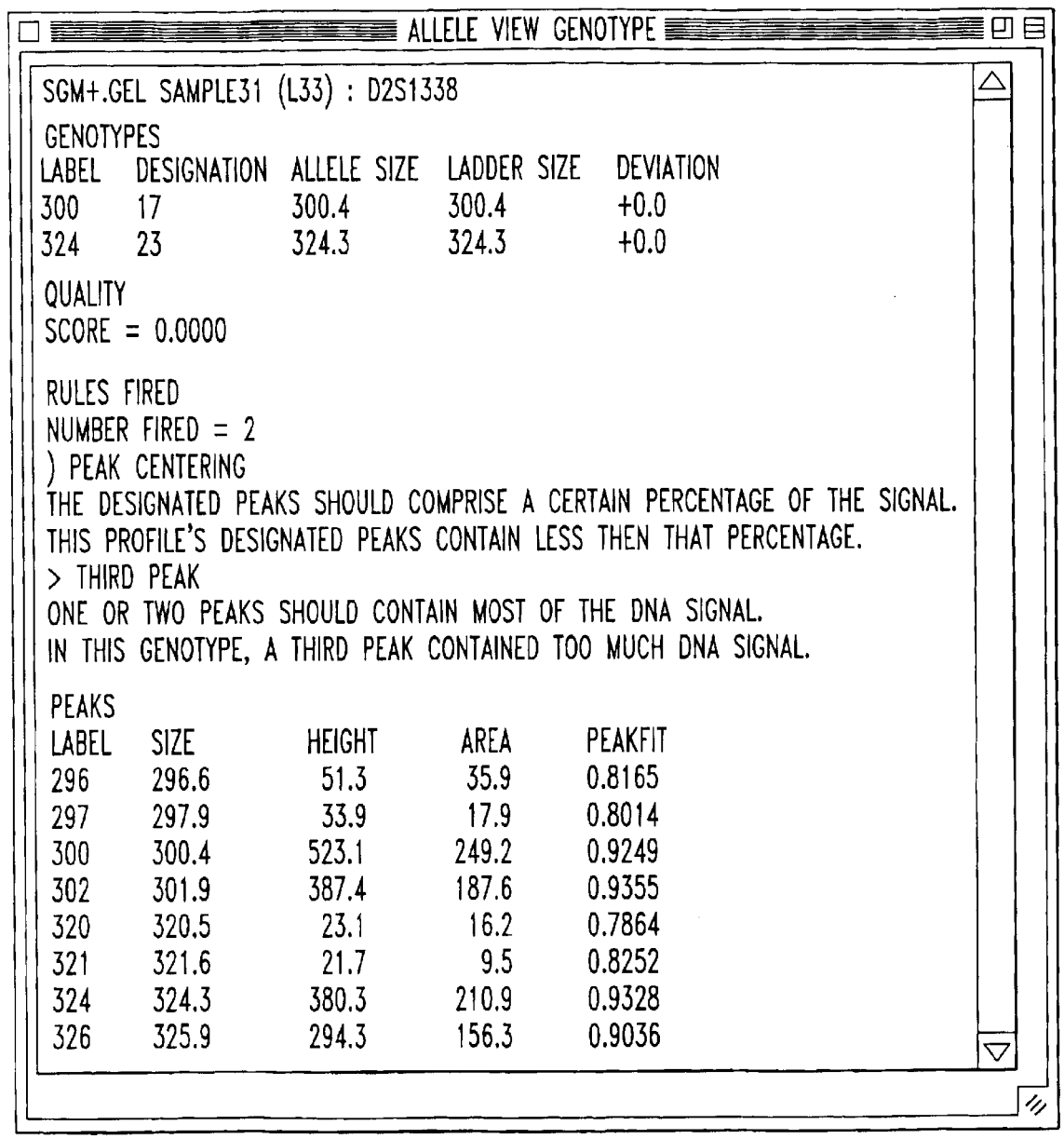
FIG. 8 shows a textual interface for displaying useful genotype results.

Referring to FIG. 8, it is also useful to present the results textually. Textual information can facilitate a more detailed understanding of a particular experiment. It is helpful for the user to have rapid access to both graphical and text presentation formats. The preferred embodiment provides information on allele designations, ladder comparisons, molecular weight sizes, and genotype quality. This display also gives explanations of rules that may have fired. The table includes peak size, peak height, peak area, and peak fit quality. The display is extensible, permitting modifications to the display that can draw from the expected and observed values that are computed for each scored genotype.

The preferred embodiment provides very flexible navigation between the graphical and textual view. A gel display permits viewing of any combination of gel image, size standard peak centers, or lane/size tracking grid, as well as editing capability. An allele call display provides navigation facilities (e.g., buttons and menus) for rapidly selecting samples and loci, including zoom, slider, overlay, and relational options. With a single click, the user can examine the peak and ladder sizes of any designated allele. The interface also automates many of the mundane display aspects (e.g., signal resizing, quality prioritization), thereby enabling rapid user navigation.

For maximum flexibility, the preferred embodiment reports results to computers and people in multiple ways. Preferred modalities include:

Providing a flexible format (e.g., tabbed text files, or SQL queries) for seamless interaction with database, spreadsheet, laboratory information management system (LIMS), text editing, and other computer software.

Providing such a flexible format for input information.

Providing such a flexible format for output results.

Providing such a flexible format for logging, audit, and error messages.

Recording rule firings and quality scores (along with allele calls) in result files (e.g., tabbed text) in such a flexible format. The rule firing representation is extensible and backwardly compatible, so that it is easy to add more rules over time as more cases are observed.

When a window focused on a genotype, displaying the fired rules (if any), thereby setting the context for why particular low quality data were rejected.

Listing or explaining the fired rules in plain English in a textual window for the human operator.

Listing the designations, allelic ladder information, molecular weight deviations (between the designation and its allelic ladder), quality score, or a table of peak sizes, areas, heights, and qualities.

Different data artifacts are typically associated with their own specific visualizations. For example, a signal containing size-designated standard peaks do not overlay properly on a different signals' size-designated standard peaks; referring to FIG. 9, this improper overlay can be visualized by superimposing the signals in different colors. For most data artifacts, human data reviewers painstakingly (a) contruct an appropropriate visual representation (e.g., an overlay of specific signals) to (b) confirm or disconfirm the presence of the artifact. The more efficient approach of the preferred embodiment is to reverse this order. First (b), have the computer automatically determine (from rules or other quality scores) what data artifacts are present, and then (a) automatically construct visualizations that are customized to each specific artifact. These data-directed visualizations can be opened up automatically, or displayed upon request.

Figure 9:
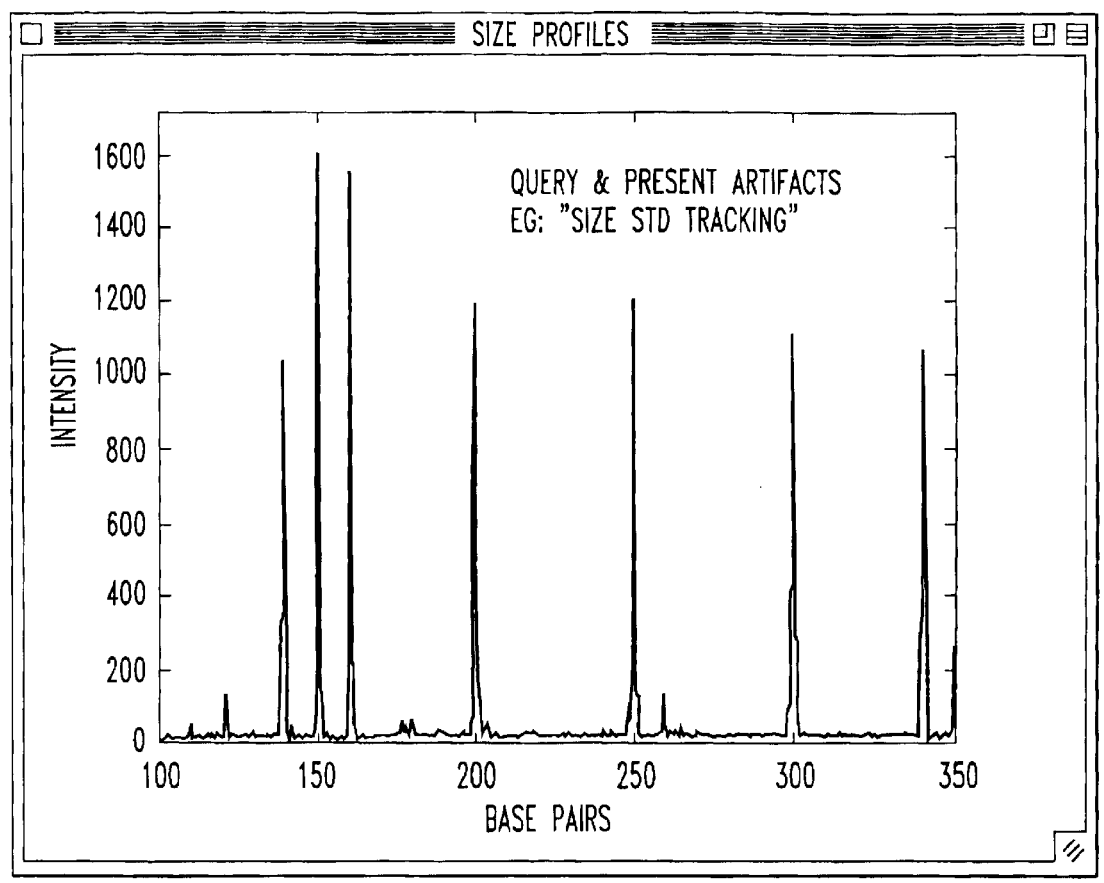
FIG. 9 shows a visualization that is customized to a data artifact.

Referring to FIGS. 4, 6, and 9, to efficiently develop a library of such data artifact customized displays, the invention includes a graphical language interpreter. An element of the display library is a message template that operationally characterizes how to display the artifact. This template is filled in by applying it to specific data. A message for the interpreter includes a set of n-tuples that describe the type of display, the source of data, a size range, fluorescent dye, or other useful display information. The data source preferably refers to the n×k representation of data signals. This interpreter then dispatches on the display type (e.g., data signal, vertical line, fitted curve, annotation, etc.) and possible subtype (e.g., main data, size ladder, allelic ladder, known control, negative control, etc.) of each tuple to supply additional display information (e.g., drawing color, line style, line thickness, etc.) that is specific to that display type. Execution of the set of messages contructs and presents the customized display to the user for its corresponding data artifact.

Analysis System

Figure 10:
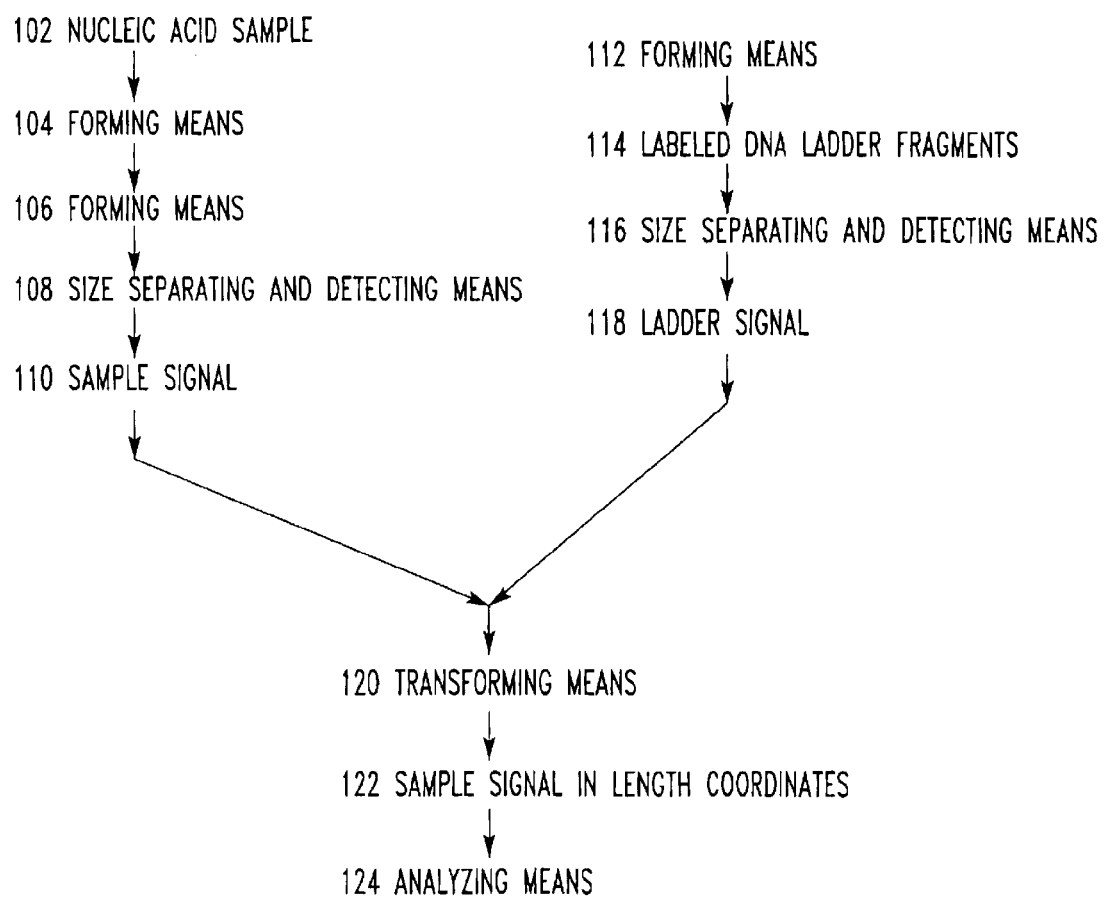
FIG. 10 shows a system for analyzing a nucleic acid sample.

Referring to FIG. 10, the present invention pertains to a system for analyzing a nucleic acid sample 102, as specified above. The system comprises a means 104 for forming labeled DNA sample fragments 106 from a nucleic acid sample. The system further comprises means 108 for size separating and detecting said sample fragments to form a sample signal 110, said separating and detecting means in communication with the sample fragments. The system further comprises means 112 for forming labeled DNA ladder fragments 114 corresponding to molecular lengths. The system further comprises means 116 for size separating and detecting said ladder fragments to form a ladder signal 118, said separating and detecting means in communication with the ladder fragments. The system further comprises means 120 for transforming the sample signal into length coordinates 122 using the ladder signal, said transforming means in communication with the signals. The system further comprises means 124 for analyzing the nucleic acid sample signal in length coordinates, said analyzing means in communication with the transforming means.

Special Applications

For many applications, it is useful to generate sizing results that are comparable across different DNA sequencer instruments. This platform interoperability is essential, for example, when creating a reference DNA database (e.g., for human identification in forensics, or multi-laboratory genetic analyses) with data comparisons from multiple laboratories. Should different instruments at different laboratories yield different sizing results for PCR products relative to the size standards, then such DNA reference resources become almost useless. The present invention uses sizing ladders based on such sample fragments (e.g., allelic ladders, with or without known reference samples) in order to assure that sizing results are based on sample fragment sizes. Specifically, said sizing results are not based solely on electrophoretic migration of DNA fragments relative to size standard moledules; such relative migration can be highly variable across different instruments, and even on the same instrument when different run conditions are employed. The present invention overcomes this limitation in the current art, uses novel computer-based scoring of properly calibrated data to provide automated sizing of DNA fragments, and enables true interoperability between different sizing instruments.

Via this interoperability, the invention provides a method for producing a nucleic acid analysis. Steps include: (a) analyzing a first nucleic acid sample on a first size separation instrument to form a first signal; (b) analyzing a second nucleic n acid sample on a second size separation instrument to form a second signal; (c) comparing the first signal with the second signal in a computing device with memory to form a comparison; and (d) producing a nucleic acid analysis of the two samples from the comparison that is independent of the size separation instruments used.

In forensic applications, it useful to match a sized-based genotype (e.g., STR or SNP) of a sample against a reference genotype. In making such forensic match comparisons, it is preferable to have a computer scoring program designate alleles relative to an allelic ladder, rather than using an "exact" size relative to sizing standards. This is because of the highly variable differential migration of the sizing standards relative to the PCR products. An allelic ladder (whether precharacterized or dynamically characterized) provides standard reference DNA molecule lengths. By comparing and reporting sample DNA fragment lengths relative to these constant reference DNA lengths (and not to variable size standard comigration units), it is possible to reliably match genotypes of a given sample with those of a reference sample. This comparison and reporting is enabled by the present invention. Moreover, this reliability is essential for human identification applications where near zero error is required. In criminal comparisons, the sample DNA profile may be from a stain at a crime scene, whereas the reference DNA profile is from a suspect or a preexisting DNA database, with the goal of establishing a connection between a suspect and a crime scene. In civil applications, the sample and reference DNA profiles may be used to determine degree of relatedness, as in a paternity case. (I W Evett and B S Weir, Interpreting DNA Evidence Statistical Genetics for Forensic Scientists. Sunderland, Mass.: Sinauer Assoc, 1998), incorporated by reference.

PCR artifacts can complicate DNA fragment sizing. With STRs, PCR stutter, relative amplification (also termed "preferential amplification"), and constant bands are common artifacts. Using computer-based scoring methods, these artifacts can be resolved by stutter deconvolution, adjusting relative peak heights based on fragment size, detecting and suppressing artifactual bands, and other quantitative methods. (M W Perlin, "Method and system for genotyping," U.S. Pat. No. 5,541,067, Jul. 30, 1996; M W Perlin, "Method and system for genotyping," U.S. Pat. No. 5,580,728, Dec. 3, 1996; S-K Ng, "Automating computational molecular genetics: solving the microsatellite genotyping problem," Carnegie Mellon University, Doctoral dissertation CMU-CS-98-105, Jan. 23, 1998), incorporated by reference.

Differential display is a sensitive assay for relative gene expression. In automated computer data analysis of differential display gene expression profiles, the objective is to identify size bins at which there is a demonstrable difference between the DNA amounts present in the two profiles. In a preferred embodiment, to compare:

Transform the expression profiles so that each resides in a uniform DNA sizing coordinate system, referring to FIG. 1, Step 6. When the pixel representation is highly reproducible (e.g., when running serially on a single capillary), this transforming step can be omitted.

Identify the peaks in each profile, and record their x domain (DNA size) and y height (estimated DNA concentration) values.

Compare the domain values of the peaks in each profile, and form a set of matching paired peaks (one from each profile). Retain those paired peaks with close x values. In the preferred embodiment, the difference between the x values is less than or equal to ½ base pair.

Retain the cross-profile peak pairs having relatively close y value ratios. Compute the standard deviation of the ratio of the y values for peak pairs, and remove those peak pairs whose y-value ratios lie outside a certain standard deviation range (e.g., one standard deviation).

Rescale the profile ranges so that they approximately superimpose. Normalize the first profile by dividing by its maximum y value. Model the y-value ratios polynomially (e.g., linearly) as a function of x. Normalize the second profile by dividing by the modeled y-value ratio function.

Refine the peak matching by a two dimensional comparison that requires the matching peak pairs to satisfy both a certain x-tolerance (e.g., 0.5 bp) and certain y tolerance (e.g., 5% relative height). When the 1D peak matching does not produce spurious results, this refining step may be omitted.

Use the matched peaks as a peak ladder, and transform the coordinates of one profile into the coordinates of the second profile, referring to FIG. 1, Step 8. When the peaks are very close (preferably less than 0.25 bp deviation), this transforming step may be omitted.

Compare the superimposed profiles, and identify peak pairs whose calculated y-value differences or ratios are outliers, relative to the paired y value standard deviations. These outlying peak pairs represent possibly significant up- or down-regulation of gene expression.

Report the identified outlying peak pairs. This can be done as two lists (one for up-regulation, and one for down-regulation). Within each list, rank the results by the y value deviation.

Figure 11:
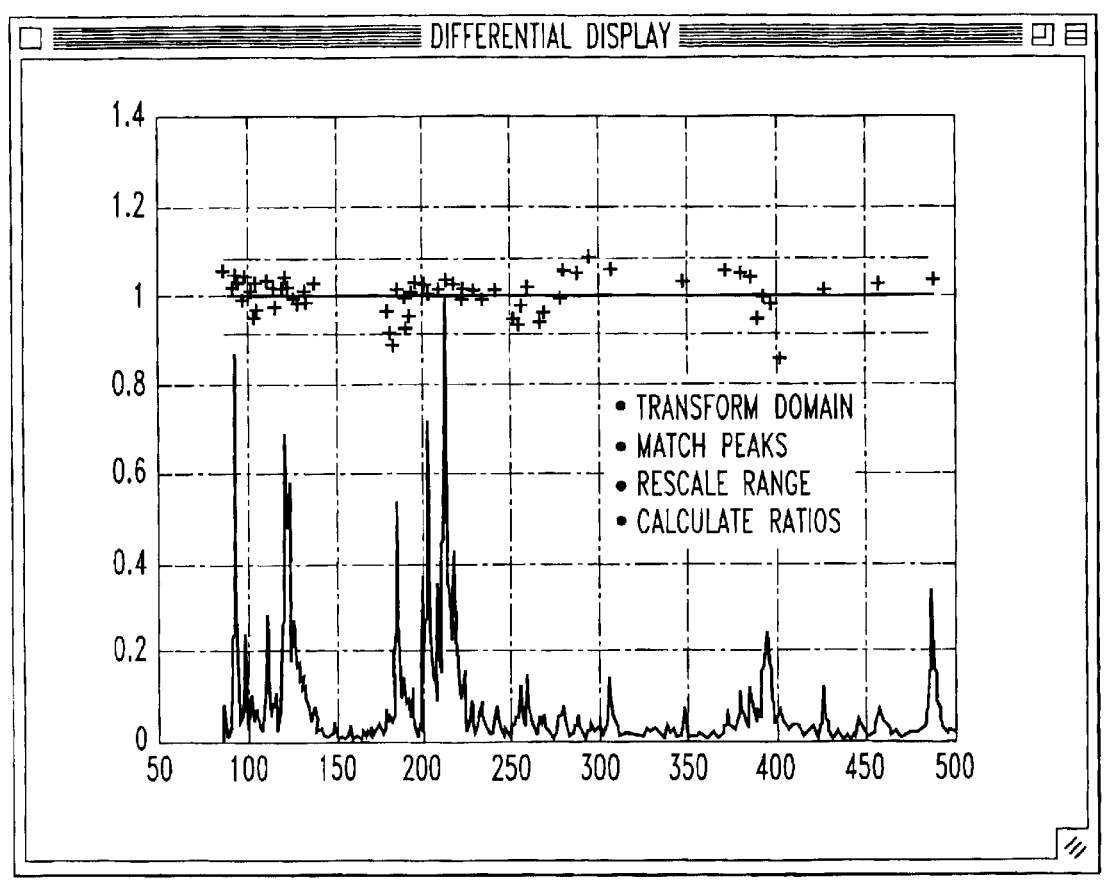
FIG. 11 shows the result of a differential display gene expression analysis.

The results of such an analysis are shown in FIG. 11, which n demonstrates no evident variation in the repeated running of one differential display sample.

Software Description

Figure 12:
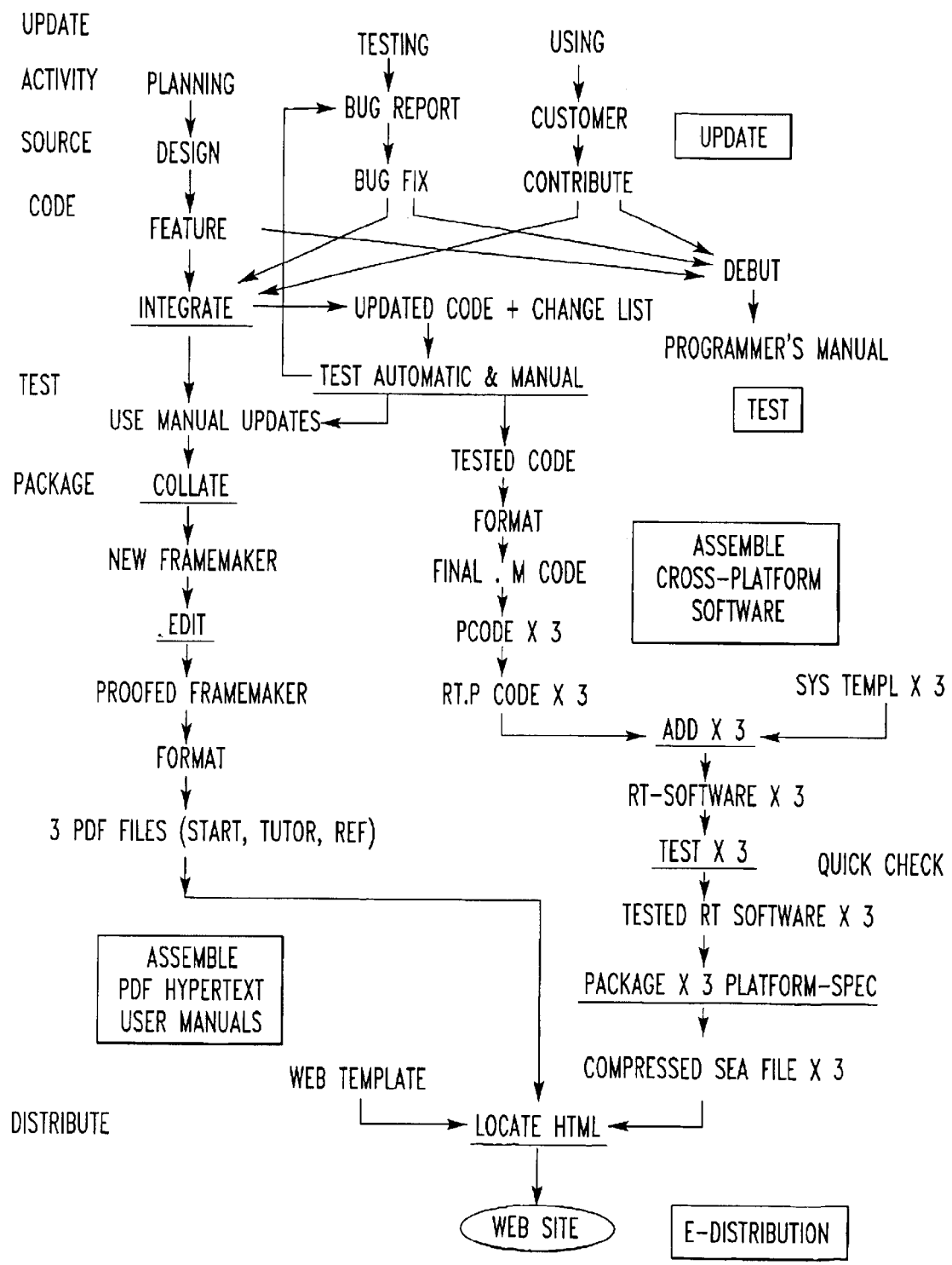
FIG. 12 shows the flow graph of automated software assembly.

Referring to FIG. 12, the data scoring software is preferably maintained in a version control system. After testing at has completed, program changes are committed. For each supported platform (Macintosh, Windows, Unix, etc.), an automated assembly computer retrieves the updated software and supporting data from the version control server, preferably over a computer network. Then, this computer compiles the software and data for run time operation on the specific target platform, and follows automation scripts to assemble the materials into an installer process, preferably for CD-ROMs or internet installation (e.g., MindVision's VISE for the Macintosh, or InstallShield for Windows). Hypertext documentation for the software is maintained, updated, and compiled in a cross-platform format, such as bookmarked PDF files, preferably using automated document authoring software (e.g., Adobe's FrameMaker program). For each supported platform, the application program, associated data, and documentation are included on the web or disk installers. Users preferably download or update their software using the web internet installer; alternatively, a disk installer can be used locally on a computer or local area network.

The automated scoring software maintains an audit trail of its actions, operation, and decisions as it processes the data according the steps of FIGS. 1 and 5. The data formats are kept operational for specific platforms by automatically checking and transforming certain files (e.g., text representations) prior to the program's using these files on that platform. The data format permits multiple instrument data acquisition runs (e.g., gel or capillary loadings) to be processed together in a single computer analysis run. These software features reduce human intervention and error.

User feedback on the program's operation is preferably entered at a designated web site onto a reporting HTML form that includes expected and observed program behavior. Via CGI sripts, these reports are automatically logged onto a database (e.g., FileMaker Pro on a Macintosh over a local area network), and appropriate personnel may be automatically notified via email of potential problems.

Business considerations

The automated quality maintenance system described herein for generating and analyzing DNA fragment data has a nonobvious business model. It is desirable for groups to generate and analyze their own data, since the users of the data often have the greatest incentive to maintain data quality. Moreover, people involved in the data generation task require continual feedback from the data analysis results. By generating data that includes proper calibration reference standards (e.g., internal size standards, allelic ladders, reference traces, etc.), high quality data can be automatically analyzed in ways that lower quality data cannot.

The cost of manual scoring of data is quite high. The preferred business model includes a spreadsheet that permits an end-user to calculate their labor costs. Referring to FIG. 13, a prospective or current customer can enter parameters related to the cost of labor, the data generation throughput, and how effectively the labor force analyzes the generated data. From these factors, the spreadsheet can calculate the total labor cost, as well as the labor cost per experiment, for the specific customer requirements. This calculating tool is preferably made available to customers in spreadsheet form (e.g., as a platform-independent Microsoft Excel 98 spreadsheet) as a computer file that can be distributed on disk, via email attachment, or downloadable from the internet. In a complementary embodiment, the spreadsheet functionality can be provided as an interative form on a web page. By better understanding the labor costs of data scoring, a customer can develop insight into the role of quality data and automated computer-based data scoring as a direct replacement for labor.

Error is another significant cost in the human scoring of genetic data. In genetics, error severely compromises the power of linkage and other association measures, so that despite considerable research time, cost, and effort, genes are less likely to be discovered. In forensics, error can lead to incorrect identification of suspects, failed convictions of criminals, or failure in exonerating the innocent. Thus, methods that reduce error or improve data quality confer significant advantages to the user.

Since automated computer-based scoring of DNA sizing data is equivalent to human labor that performs the same task, the pricing model of such automated scoring is preferably based on usage. A fee is charged for every genotype scored. This fee preferably includes components for intellectual property, software support, and user customizations. With very high levels of usage, some components such as user customization can be reduced in line with the associated business expense reduction.

For better market penetration, pricing levels should be set near or below the equivalent human labor cost. The result is an automated computer-based scoring process that is faster, better and cheaper than the equivalent human review of data. Specifically, the computer-based process can produce more consistent results with lower error, leading to more productive use of the scored data.

Additional services (including user training, system setup, software modifications, quality audits) are best charged separately. Preferably, there is a mandatory initial interaction with the customer group (for which the user pays) to train new users in the quality data generation and computer-based analysis process.

Quality assurance is an integral part of the process and the business model. A quality entity (e.g., a corporation) can help support this quality maintenance system (QMS). This entity can provide quality assurance by spot checking the user's data generation or scoring of the DNA fragment size data. This quality assurance can be done by (a) the entity providing the user with samples (characterized by the entity) for data generation or analysis, and then comparing the user's results with the entity's results, (b) the user providing the entity with samples (characterized by the user) for data generation or analysis, and then having the entity comparing the entity's results with the user's results, (c) a comparison of data results involving a third party, or (d) a double-blind comparison study.

The quality entity can use these quality assurance methods to conduct quality audits for different sites, and disseminate the results (e.g., by internet publication). Then, different data generation sites can compete with one another for business based on their quality and cost-effectiveness. Beyond a certain critical mass, it would be highly desirable for such DNA analysis sites to have certification provided by the quality entity on the basis of such audits. Those sites with the highest quality data and using the best automation software should be the most competitive. The quality entity can also provide a service (e.g., at regular time intervals, say annually) for quality checks on sites that desire to achieve and maintain the best possible data results.

This procedure describes a method for generating revenue from computer scoring of genetic data. The steps include: (a) supplying a software program that automatically scores genetic data; (b) forming genetic data that can be scored by the software program; (c) scoring the genetic data using the software program to form a quantity of genetic data; and (d) generating a revenue from computer scoring of genetic data that is related to the quantity. Moreover, additional process steps include: (e) defining a labor cost of scoring the quantity of genetic data when not using the software program; (f) providing a calculating mechanism for estimating the labor cost from the quantity; (g) determining the labor cost based on the quantity; and (h) establishing a price for using the software program that is related to the labor cost.

Mixture Analysis

In forensic science, DNA samples are often derived from more than one individual. With the advent of quantitative analysis of STR data, there is the possibility of computer-based analysis that can resolve these data. Specifically, there is a need to find or confirm the identity of component DNA profiles, as well as determine mixture ratios. In the preferred embodiment, the quantitation of the DNA samples is accomplished by performing Steps 1–6 of FIG. 1, and Steps 7–9 of FIG. 5. The accurate quantitation conducted in Step 9 enables accurate analysis of quantitative mixture data, and improves on the prior art that uses unmodeled peak area or peak height (GeneScan Software, PE Biosystems, Foster City, Calif.) which provide potentially inaccurate estimates of DNA concentration. The invention's quantitative mixture analysis is part of Step 10 of FIG. 5 in the case of DNA mixtures.

The present invention is distinguished over the prior art in that it uses a linear mathematical problem solving formulation that combines information across loci, and can completely integrate this information automatically on a computing device. By inherently using all the information from all the loci in the formulation, robust solutions can be achieved. The prior art uses manual or Bayesian methods on a per locus basis that entail human intervention in generating or combining partial results. Such prior forensic mixture analysis methods have been described (P Gill, R Sparkes, R Pinchin, T M Clayton, J P Whitaker, and J Buckleton, "Interpreting simple STR mixtures using allele peak area," Forensic Sci. Int., vol. 91, pp. 41–53, 1998; IW Evett, P Gill, and J A Lambert, "Taking account of peak areas when interpreting mixed DNA profiles," J. Forensic Sci., vol. 43, pp. 62–69, 1997; T M Clayton, J P Whitaker, R Sparkes, and R Gill, "Analysis and interpretation of mixed forensic stains using DNA STR profiling," Forensic Sci. Int., vol. 91, pp. 55–70, 1998), incorporated by reference.

There are different formulations of the mixture problem. With a mixture profile derived from two individuals, problems include:

verifying the mixture and computing the mixture ratio, given the profiles of both individuals;

determining the profile of one individual and the mixture ratio, given the profile of another individual; and determining the profiles of both individuals and the mixture ratio, given no other DNA profiles.

These problems can be similarly extended to a number of individuals greater than two. The STR mixture method described herein addresses all of these problem formulations.

In the PCR amplification of a mixture, the amount of each PCR product scales in rough proportion to relative weighting of each component DNA template. This holds true whether the PCRs are done separately, or combined in a multiplex reaction. Thus, if two DNA samples A and B are in a PCR mixture with relative concentrations weighted as wA and wB ($0 \leq wA, wB \leq 1$, $wA+wB=1$), their corresponding signal peaks after detection will generally have peak quantitations (height or area) showing roughly the same proportion. Therefore, by observing the relative peak proportions, one can estimate the DNA mixture weighting. Note that mixture weights and ratios are interchangeable, since the mixture weight $\frac{[A]}{[A]+[B]}$ is in one-to-one corresponce with the mixture ratio $\frac{[A]}{[B]}$.

To mathematically represent the linear effect of the DNA sample weights (wA, wB, wC, . . . ), write the linear equation:

$$p = G \times w,$$

where p is the pooled profile column vector, each column i of genotype matrix G represents the alleles in the genotype of individual i (taking allele values 0, 1, 2, with a total of 2 alleles), and w is the weight column vector that reflects the relative proportions of template DNA or PCR product. To illustrate this coupling of DNA mixture weights with predicted pool weights, if there are three individuals A, B, C represented in a mixture with weighting wA=0.5, wB=0.25, wC=0.25, and at one locus the genotypes are:

A has allele 1 and allele 2,
B has allele 1 and allele 3, and
C has allele 2 and allele 3, then combining the vectors via the linear equations:

$$\begin{bmatrix} \text{alleles} \\ \text{in} \\ \text{mixture} \end{bmatrix} = \begin{bmatrix} \begin{bmatrix} \text{alleles} \\ \text{of} \\ A \end{bmatrix} \begin{bmatrix} \text{alleles} \\ \text{of} \\ B \end{bmatrix} \begin{bmatrix} \text{alleles} \\ \text{of} \\ C \end{bmatrix} \end{bmatrix} \times \begin{bmatrix} wA \\ wB \\ wC \end{bmatrix}$$

and representing each allele as a position in a column vector, produces the linear relationship:

$$\begin{bmatrix} 0.75 \\ 0.75 \\ 0.50 \end{bmatrix} = \begin{bmatrix} \begin{bmatrix} 1 \\ 1 \\ 0 \end{bmatrix} \begin{bmatrix} 1 \\ 0 \\ 1 \end{bmatrix} \begin{bmatrix} 0 \\ 1 \\ 1 \end{bmatrix} \end{bmatrix} \times \begin{bmatrix} 0.50 \\ 0.25 \\ 0.25 \end{bmatrix}$$

Note that the sum of alleles in each allele column vector is normalized to equal two, the number of alleles present.

With multiple loci, the weight vector w is identical across all the loci, since that is the underlying mixture in the DNA template. This coupling of loci can be represented in the linear equations by extending the column vectors p and G with more allele information for additional loci. To illustrate this coupling of DNA mixture weights across loci, add a second locus to the three individuals above, where at locus two the genotypes are:

A has allele 1 and allele 2,
B has allele 2 and allele 3, and
C has allele 3 and allele 4, then combining the vectors via the partitioning:

$$\begin{bmatrix} \text{locus1} \\ \text{mixture} \\ \text{alleles} \\ ---- \\ \text{locus2} \\ \text{mixture} \\ \text{alleles} \end{bmatrix} = \begin{bmatrix} \begin{bmatrix} \text{locus1} \\ A\text{'s} \\ \text{alleles} \\ --- \\ \text{locus2} \\ A\text{'s} \\ \text{alleles} \end{bmatrix} \begin{bmatrix} \text{locus1} \\ B\text{'s} \\ \text{alleles} \\ --- \\ \text{locus2} \\ B\text{'s} \\ \text{alleles} \end{bmatrix} \begin{bmatrix} \text{locus1} \\ C\text{'s} \\ \text{alleles} \\ --- \\ \text{locus2} \\ C\text{'s} \\ \text{alleles} \end{bmatrix} \end{bmatrix} \times \begin{bmatrix} wA \\ wB \\ wC \end{bmatrix}$$

and representing each allele as a position in a column vector, produces:

$$\begin{bmatrix} 0.75 \\ 0.75 \\ 0.50 \\ -- \\ 0.50 \\ 0.75 \\ 0.50 \\ 0.25 \end{bmatrix} = \begin{bmatrix} \begin{bmatrix} 1 \\ 1 \\ 0 \\ - \\ 1 \\ 1 \\ 0 \\ 0 \end{bmatrix} \begin{bmatrix} 1 \\ 0 \\ 1 \\ - \\ 0 \\ 1 \\ 1 \\ 0 \end{bmatrix} \begin{bmatrix} 0 \\ 1 \\ 1 \\ - \\ 0 \\ 0 \\ 1 \\ 1 \end{bmatrix} \end{bmatrix} \times \begin{bmatrix} 0.50 \\ 0.25 \\ 0.25 \end{bmatrix}$$

With multiple loci, there is more data and greater confidence in estimates computed from the linear equations.

More precisely, write the vector/matrix equation $p = G \times w$ for mixture coupling (of individual and loci) as coupled linear equations that include the relevant data:

$$p_{ik} \sum_j g_{ijk} w_j,$$

where for locus i, individual j, and allele k
  $P_{ik}$ is the pooled proportion in the observed mixture of locus i, allele k;
  $g_{ijk}$ is the genotype of individual j at locus i in allele k, taking values 0 (no contribution), 1 (heterozyote or hemizygote contribution), or 2 (homozygote contribution), though with anomalous chromosomes other integer values are possible; and
  $w_j$ is the weighting in the mixture of individual j.

Given partial information about equation $p=G \times w$, other elements can be computed by solving the equation. Cases include:
  When G and w are both known, then the data profile p can be predicted. This is useful in search algorithms.
  When G and p are both known, then the weights w can be computed. This is useful in confirming a suspected mixture, and in search algorithms.
  When p is known, inferences can be made about G and w, depending on the prior information available (such as partial knowledge of G). This is useful in human identification applications.

The DNA mixture is resolved in different ways, depending on the case.

Assume throughout that the mixture profile data vector p has been normalized for each locus. That is, for each locus, let NumAlleles be the number of alleles found in data for that locus (typically NumAlleles=2, one for each chromosome). For each allele element of the quantitation data within the locus, multiply by NumAlleles, and divide by the sum (over the alleles) of all the quantitation values for that locus. Then, the sum of the normalized quantitation data is NumAlleles, as in the illustrative example above.

To resolve DNA mixtures, perform the steps: (a) obtain DNA profile data that include a mixed sample; (b) represent the data in a linear equation; (c) derive a solution from the linear equation; and (d) resolve the DNA mixture from the solution. This procedure is illustrated in the following cases.

First consider the case where all the genotypes G and the mixture data p are known, and the mixture weights w need to be determined. This problem is resolved by solving the linear equations $p = G \times w$ for w using SVD or some other matrix inversion method. Specifically, w can be estimated as:

$$w = G \backslash p$$

using the SVD matrix division operation in MATLAB.

Next consider the case of two individuals A and B where one of the two genotypes (say, A) is known, the mixture weights w are known, and the quantitative mixture data profile p is available. Expand $p = G \times w$ in this case as:

$$p = wA \cdot gA + wB \cdot gB$$

where gA and gB are the genotype column vectors of individuals A and B, and wA and $wB = (1 - wA)$ are their mixture weights. Then, to resolve the genotype, rewrite this equation as $$gB = (p - wA \cdot gA)/wB$$

and solve for gB by matrix operations. The computed gB is the normalized difference of the mixture profile minus A's genotype. The accuracy of the solution increases with the number of loci used, and the quality of the quantitative data.

Next consider the case of making inferences about the genotype matrix G starting from a mixture profile p. This case has utility in forensic science. In one typical scenario, a stain from a crime scene may contain a DNA mixture from the victim and an unknown individual, the victim's DNA is available, and the investigator would like to connect the unknown individual's DNA profile with a candidate perpetrator. This scenario typically occurs in rape cases. The perpetrator may be a specific suspect, or the investigator may wish to check the unknown individual's DNA profile against a DNA database of possible candidates. If the mixture weight wA were known, then the genotype gB could be computed immediately from the matrix difference operation of the preceding paragraph.

Since wA is not known, a workable approach is to search for the best w in the [0,1] interval that satisfies additional constraints on the problem, set wA equal to this best w, compute the genotype g(wA) as a function of this optimized wA value, and set $gB = g(wA)$. A suitable constraint is the prior knowledge of the form that possible solution genotype vectors g can take. It is known that solutions must have a valid genotype subvector at each locus (e.g., having alleles taking on values 0, 1 or 2, and summing to 2). This knowledge can be translated into a heuristic function of g(w) which evaluates each candidate genotype solution g against this criterion.

In the preferred embodiment, the heuristic is a function of w, the profile p, and the known genotype gA. Since p and gA are fixed for any given problem, in this case the function depends only on the variable w. For any given w in (0,1), compute g(w) as $(p - w \cdot gA)/(1 - w)$. Then, at each locus, compute and record the deviation $dev_{locus}(g(w))$. The $dev_{locus}$ function at one locus is defined as:

Assume the genotype comprises one allele. Compute the deviation by finding the index of the largest peak, and forming a vector oneallele that has the value 2 at this index and is 0 elsewhere. Let dev1 be the $L_2$ norm of the difference between g(w) and oneallele.

Assume the genotype comprises two alleles. Compute the deviation by finding the index of the two largest peaks, and forming a vector twoallele that has the value 1 at each of these two indices and is 0 elsewhere. Let dev2 be the $L_2$ norm of the difference between g(w) and twoallele.

Return the the lesser of the two deviations as minimum (dev1, dev2).

To compute dev(g(w)), sum the component $dev_{locus}(g(w))$ at each locus. That is, the heuristic function is the scalar value $$dev(g(w)) = \sum_{loci} dev_{locus}(g(w))$$

Appropriately optimize (e.g., minimize) this function over w in [0,1] to find wB, and determine gB as g(wB). In one alternative preferred embodiment, the summation terms can be normalized to reflect alternative preferred weightings of the loci or alleles. In a different alternative preferred embodiment, various heuristic functions can be used that reflect other reasonable constraints on it the genotype vectors, as in (P Gill, R Sparkes, R Pinchin, T M Clayton, J P Whitaker, and J Buckleton, "Interpreting simple STR mixtures using allele peak area," Forensic Sci. Int., vol. 91, pp. 41–53, 1998), incorporated by reference.

Referring to Step 10 of FIG. 5, further quality assessment can be performed on the computed STR profile derived from the mixture analysis. As described, rule checking can identify potentially anomalous allele calls, particularly when peak quantities or sizes do not conform to expectations. Quality measures can be computed on the genotypes, which can indicate problematic calls even when no rule has fired. One preferred quality score in mixture analysis is the deviation dev(gb) of the computed genotype. Low deviations indicate a good result, whereas high scores suggest a poor result. These deviations are best interpreted when scaled relative to a set of calibration data which have been classified as correct or incorrect. Of particular utility is the partitioning of the deviations by locus, using the locus deviation function $dev_{locus}(gB)$. When a locus has an unusually high deviation, it can be dropped from the profile, and the resulting partial profile can be used for human identity matching.

Figure 14:
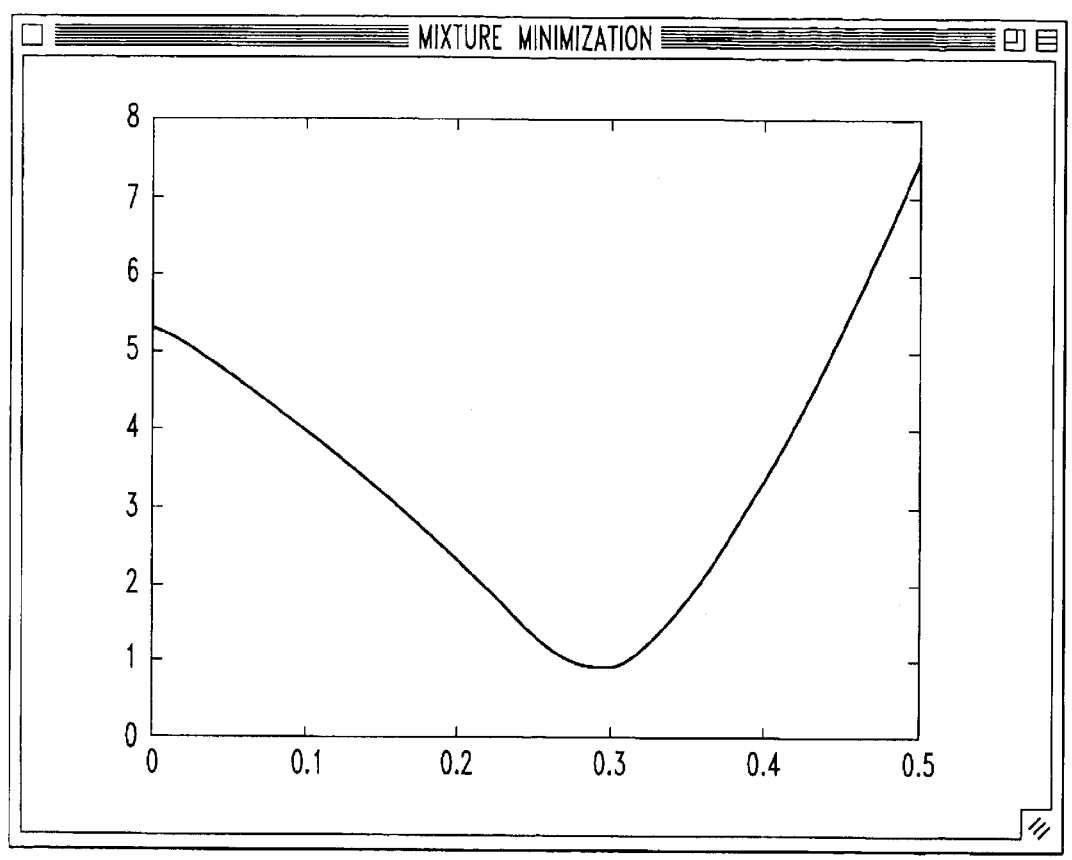
FIG. 14 shows a heuristic function dev(g(w)) which has an umbiguous local minimum.

The most preferred embodiment is demonstrated here on data generated using the 10 STR locus SGMplus panel (PE BioSystems, Foster City, Calif.), and size separated and detected on an ABI/310 genetic analyzer sequencing instrument. A mixture proportion of 30% sample A and 70% sample B was used. Referring to FIG. 14, a minimization search for weight w by computing dev(g(w)) gave a weighting of 29.73%, which is very close to the true 30%. The $L_2$ deviation dev(g(w)) of the computed genotype from the closest (and correct) feasible solution was 0.3199. The computed genotype for all the loci is shown in the columns PROFILE (exact) and GENO B (rounded) in the table below.

Data and results are shown in the table below, where MIXTURE is the normalized peak quantitation data from the mixed sample, GENO A is the known genotype of individual A, PROFILE is the numerical genotype computed for determining B's genotype, GENO B is the resulting integer genotype (and, in this case, the known genotype as well), and DEVS are the square deviations of the PROFILE from GENO B. Quality assessment of the computed PROFILE shows uniform peaks that are consistent with a correct genotype. Examination of the square deviation components for each allele reveals no significant problem, and the largest within locus sum of squares deviation was the small value 0.16 (for locus D21S11).

| LOCUS-ALLELE | MIXTURE | GENO A | PROFILE | GENO B | DEVS |
|---|---|---|---|---|---|
| D3S1358-14 | 1.0365 | 1.0000 | 1.0520 | 1.0000 | 0.0027 |
| D3S1358-15 | 0.9635 | 1.0000 | 0.9480 | 1.0000 | 0.0027 |
| vWA-17 | 1.4755 | 0 | 2.0999 | 2.0000 | 0.0100 |
| vWA-18 | 0.5245 | 2.0000 | −0.0999 | 0 | 0.0100 |
| D16S539-11 | 1.4452 | 0 | 2.0567 | 2.0000 | 0.0032 |
| D16S539-13 | 0.2889 | 1.0000 | −0.0120 | 0 | 0.0001 |
| D16S539-14 | 0.2660 | 1.0000 | −0.0447 | 0 | 0.0020 |
| D2S1338-16 | 0.3190 | 1.0000 | 0.0308 | 0 | 0.0010 |
| D2S1338-18 | 0.6339 | 0 | 0.9021 | 1.0000 | 0.0096 |
| D2S1338-20 | 0.3713 | 1.0000 | 0.1052 | 0 | 0.0111 |
| D2S1338-21 | 0.6758 | 0 | 0.9618 | 1.0000 | 0.0015 |
| D8S1179-9 | 0.7279 | 0 | 1.0359 | 1.0000 | 0.0013 |
| D8S1179-12 | 0.2749 | 1.0000 | −0.0320 | 0 | 0.0010 |
| D8S1179-13 | 0.6813 | 0 | 0.9696 | 1.0000 | 0.0009 |
| D8S1179-14 | 0.3160 | 1.0000 | 0.0265 | 0 | 0.0007 |
| D21S11-27 | 0.2787 | 1.0000 | −0.0265 | 0 | 0.0007 |
| D21S11-29 | 0.7876 | 0 | 1.1208 | 1.0000 | 0.0146 |
| D21S11-30 | 0.9337 | 1.0000 | 0.9057 | 1.0000 | 0.0089 |
| D18S51-12 | 0.3443 | 1.0000 | 0.0669 | 0 | 0.0045 |
| D18S51-13 | 0.6952 | 0 | 0.9894 | 1.0000 | 0.0001 |
| D18S51-14 | 0.6755 | 0 | 0.9613 | 1.0000 | 0.0015 |
| D18S51-17 | 0.2850 | 1.0000 | −0.0176 | 0 | 0.0003 |
| D19S433-12.2 | 0.6991 | 0 | 0.9949 | 1.0000 | 0.0000 |
| D19S433-14 | 0.6060 | 2.0000 | 0.0161 | 0 | 0.0003 |
| D19S433-15 | 0.6949 | 0 | 0.9890 | 1.0000 | 0.0001 |
| THO1-6 | 0.3178 | 1.0000 | 0.0291 | 0 | 0.0008 |
| THO1-7 | 1.0074 | 1.0000 | 1.0105 | 1.0000 | 0.0001 |
| THO1-9 | 0.6749 | 0 | 0.9605 | 1.0000 | 0.0016 |
| FGA-19 | 1.0580 | 1.0000 | 1.0826 | 1.0000 | 0.0068 |
| FGA-24 | 0.2830 | 1.0000 | −0.0203 | 0 | 0.0004 |
| FGA-25.2 | 0.6589 | 0 | 0.9378 | 1.0000 | 0.0039 |

In an alternative preferred embodiment, the heuristic function can be extended to account for the curvature of deviations (as a function of w), so that only local minima are considered and not boundary points. Genotype elimination constraints can be applied when there is extra knowledge, such when the mixture weight (hence proportion of sample B) is low and sample A's genotype can be excluded in certain cases. It is also possible to provide for interactive human feedback, so that expert assessments can work together with the computing method.

When stutter peaks are a concern, use stutter deconvolution to mathematically remove the stutter artifact from the quantitative signal (M W Perlin, G Lancia, and S-K Ng, "Toward fully automated genotyping: genotyping microsatellite markers by deconvolution," Am. J. Hum. Genet., vol. 57, no. 5, pp. 1199–1210, 1995), incorporated by reference. The prior forensic art uses Bayesian approaches to account for stutter (P Gill, R Sparkes, and J S Buckleton, "Interpretation of simple mixtures when artefacts such as stutters are present—with special reference to multiplex STRs using by the Forensic Science Service," Forensic Sci. Int., vol. 95, pp. 213–224, 1998), incorporated by reference. However, direct stutter removal from the signal can be highly robust, since it is working directly at the level of the stutter artifact, prior to any mixture computation.

In the case when both genotypes are unknown, use additional search. Start from the linear equations p=G×w. As necessary, form feasible submatrices H(locus) of G, where each H is an K×2 matrix, representing K alleles (rows) for 2 individuals (columns). Here, H={$g_{ijk}$}, where locus i is fixed, individual j ∈{1,2}, and allele k∈{1, 2, . . . , K}. For example, the six feasible four allele (K=4) genotype pairs are represented by the six genotype matrices {$H_i$|i=1, 2, . . . , 6}:

$$H = \begin{bmatrix} g_{*11} & g_{*21} \\ g_{*12} & g_{*22} \\ g_{*13} & g_{*23} \\ g_{*14} & g_{*24} \end{bmatrix} \in \left\{ \begin{bmatrix} 1 & 0 \\ 1 & 0 \\ 0 & 1 \\ 0 & 1 \end{bmatrix}, \begin{bmatrix} 1 & 0 \\ 0 & 1 \\ 1 & 0 \\ 0 & 1 \end{bmatrix}, \begin{bmatrix} 1 & 0 \\ 0 & 1 \\ 0 & 1 \\ 1 & 0 \end{bmatrix}, \begin{bmatrix} 0 & 1 \\ 1 & 0 \\ 1 & 0 \\ 0 & 1 \end{bmatrix}, \begin{bmatrix} 0 & 1 \\ 1 & 0 \\ 0 & 1 \\ 1 & 0 \end{bmatrix}, \begin{bmatrix} 0 & 1 \\ 0 & 1 \\ 1 & 0 \\ 1 & 0 \end{bmatrix} \right\}$$

Matrix division (e.g., SVD) is performed using these H submatrices. The mixture profile data at each individual locus p(locus) is also used. Proceed as follows:

1. Normalize the mixture data p to sum to 2 at each locus.
2. Find the best two element weighting vector w. On the subset of most informative loci (typically those loci having four allele loci):
   For each locus,
      For every valid genotype submatrix H at that locus,
         compute w(locus,H)=p(locus)\H
         normalize w(locus,H) to sum to 1
         set dev(locus,H) to norm{p(locus)−H×w(locus,H)'}
   Set w=w(locus,H) having the smallest dev(locus,H).
3. Derive the genotype H of each locus as follows:
   For every valid genotype matrix $H_i$ at that locus,
      compute dev($H_i$)=norm{p(locus)−$H_i$×w'}
   Set H(locus) to that $H_i$ having the smallest dev($H_i$).
4. Assess the quality of the genotype result G formed by combining the {H(locus)} at each locus. This is preferably done by:
   (a) using the matrix operation w=G\p to estimate a second mixture weight w, and comparing with the first w found in Step 2, or
   (b) by examining the computed deviations dev(H(locus)) found in Step 3.

Note that the operation "w(locus,H)=p(locus)\H" in this procedure for computing the best weight uses a matrix operation (i.e., matrix division). This procedure is preferable to finding w by minimizing norm{p(locus)−H×w(locus,H)} over w using brute force computation.

Herein, means or mechanism for language has been used. The presence of means is pursuant to 35 U.S.C. §112 paragraph and is subject thereto. The presence of mechanism is outside of 35 U.S.C. §112 and is not Herein, means or mechanism for language has been used. The presence of means is pursuant to 35 U.S.C. §112 paragraph and is subject thereto. The presence of mechanism is outside of 35 U.S.C. §112 and is not subject thereto.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:
1. A method for analyzing a DNA mixture comprised of the steps:
   (a) obtaining DNA profile data of a sample that comprises a DNA mixture of two or more individuals;
   (b) representing the data and a genotype of the individuals contained in the DNA mixture in a set of linear equations;
   (c) deriving a mathematical solution by performing a matrix operation on the linear equations; and

(d) determining the genotype at a locus of an individual contained in the DNA mixture from the mathematical solution.

2. A method as described in claim 1 wherein the obtaining step (a) includes the step of performing a PCR on an STR locus of an individual.

3. A method as described in claim 1 wherein the representing step (b) includes a matrix or vector representation of the set of linear equations.

4. A method as described in claim 3 wherein the matrix representation has a term that includes a matrix multiplication of a genotype matrix and a weight matrix.

5. A method as described in claim 1 wherein the deriving step (c) includes an optimization procedure.

6. A method as described in claim 5 wherein the optimization procedure includes a minimization step.

7. A method as described in claim 5 wherein the optimization procedure includes an arithmetic operation.

8. A method as described in claim 1 wherein the determining step (d) produces an estimate of the genotype of an individual.

9. A method as described in claim 8 wherein after the determining step (d), the estimated genotype is matched against a suspect genotype.

10. A method as described in claim 9 wherein the suspect genotype is drawn from a database of candidate suspect genotypes.

11. A method as described in claim 9 wherein the suspect is a likely perpetrator of a crime.

12. A method as described in claim 1 wherein the determining step (d) produces an estimate of a proportion or weight of an individual's DNA contained in the DNA structure.

13. A method as described in claim 1 wherein the determining step (d) produces an estimate of the quality of the determined solution.

14. A method as described in claim 1 wherein the determining step (d) jointly produces both an estimate of a proportion or weight of an individual's DNA contained in the DNA mixture and an estimate of the genotype of the individual.

* * * * *